United States Patent
Cohn et al.

(10) Patent No.: US 9,499,869 B2
(45) Date of Patent: Nov. 22, 2016

(54) MICRORNA-BASED METHODS AND COMPOSITIONS FOR THE DIAGNOSIS, PROGNOSIS AND TREATMENT OF OVARIAN CANCER USING A REAL-TIME PCR PLATFORM

(71) Applicant: The Ohio State University, Columbus, OH (US)

(72) Inventors: David E. Cohn, Bexley, OH (US); Kimberly E. Resnick, Shaker Hts., OH (US); Hansjuerg Alder, Columbus, OH (US); Carlo M. Croce, Columbus, OH (US)

(73) Assignee: The Ohio State University, Columbus, OH (US)

( * ) Notice: Subject to any disclaimer, the term of this patent is extended or adjusted under 35 U.S.C. 154(b) by 17 days.

(21) Appl. No.: 14/284,992

(22) Filed: May 22, 2014

(65) Prior Publication Data

US 2014/0256591 A1    Sep. 11, 2014

Related U.S. Application Data

(63) Continuation of application No. 13/132,583, filed as application No. PCT/US2009/038214 on Mar. 25, 2009, now abandoned.

(60) Provisional application No. 61/120,123, filed on Dec. 5, 2008.

(51) Int. Cl.
| | | |
|---|---|---|
| *C12Q 1/68* | (2006.01) | |
| *A61K 31/7105* | (2006.01) | |
| *C12N 15/113* | (2010.01) | |

(52) U.S. Cl.
CPC ......... *C12Q 1/6886* (2013.01); *A61K 31/7105* (2013.01); *C12N 15/113* (2013.01); *C12Q 1/6809* (2013.01); *C12N 2310/113* (2013.01); *C12N 2310/141* (2013.01); *C12Q 2525/207* (2013.01); *C12Q 2600/136* (2013.01); *C12Q 2600/178* (2013.01)

(58) Field of Classification Search
None
See application file for complete search history.

(56) References Cited

PUBLICATIONS

Taylor & Gercel-Taylor in "MicroRNA signatures of tumor-derived exosomes as diagnostic biomarkers of ovarian cancer" (Gynecologic Oncology vol. 110, No. 1, pp. 13-21, Jul. 1, 2008, IDS reference).*
Resnick, Alder, Hagan, Richardson, and Croce in the detection of differentially expressed microRNAs from the serum of ovarian cancer patients using a novel real-time PCR platform (Gynecologic Oncology Jan. 2009, vol. 112, pp. 55-59).*
Australian Patent Examination Report No. 1, Application No. AU 2009322907, dated Oct. 9, 2015.
Dahiya et al., "MicroRNA Expression and Identification of Putative miRNA Targets in Ovarian Cancer", PLoS One, Jun. 2008, vol. 3, Issue 6, pp. 1 -11.
Iorio et al., "MicroRNA Signatures in Human Ovarian Cancer", Cancer Research, Sep. 2007, vol. 67, No. 18, pp. 8699-8707.
Nam et al., "MicroRNA Expression Profiles in Serous Ovarian Carcinoma", Clinical Cancer Research, May 2008, vol. 14, No. 9, pp. 2690-2695.
Resnick et al., "The detection of differentially expressed microRNAs from the serum of ovarian cancer patients using a novel real-time PCR platform", Gynecologic Oncology, 2009, vol. 112, pp. 55-59.
Shih et al., "Exosomal mircoRNAs step into the biomarker area", Gynecologic Oncology, 2008, vol. 110, pp. 1-2.
Taylor et al., "MicroRNA signatures of tumor-derived exosomes as diagnostic biomarkers of ovarian cancer", Gynecologic Oncology, 2008, vol. 110, pp. 13-21.
Zhang et al., "Genomic and epigenetic alterations deregulate microRNA expression in human epithelial ovarian cancer", Proceedings of the National Academy of Sciences USA, May 2008, vol. 105, No. 19, pp. 7004-1009.

* cited by examiner

*Primary Examiner* — Catherine S Hibbert
(74) *Attorney, Agent, or Firm* — MacMillan, Sobanski & Todd, LLC

(57) ABSTRACT

Methods and compositions for the diagnosis, prognosis and/or treatment of ovarian cancer are disclosed.

9 Claims, 1 Drawing Sheet

MICRORNA-BASED METHODS AND COMPOSITIONS FOR THE DIAGNOSIS, PROGNOSIS AND TREATMENT OF OVARIAN CANCER USING A REAL-TIME PCR PLATFORM

CROSS-REFERENCE TO RELATED APPLICATIONS

This application is a continuation application of U.S. Ser. No. 13/132,583, filed Jun. 29, 2011, which claims the benefit of PCT/US2009/038214 application filed Mar. 25, 2009, which claims priority to the U.S. Provisional Application No. 61/120,123, filed Dec. 5, 2008, the entire disclosure of which is expressly incorporated herein by reference.

STATEMENT REGARDING FEDERALLY SPONSORED RESEARCH

This invention was not made with government support and the government has no rights in this invention.

TECHNICAL FIELD AND INDUSTRIAL APPLICABILITY OF THE INVENTION

This invention relates generally to the field of molecular biology. Certain aspects of the invention include application in diagnostics, therapeutics, and prognostics of ovarian cancer related disorders.

BACKGROUND

There is no admission that the background art disclosed in this section legally constitutes prior art.

In 2008, it is expected that 20,180 women will be diagnosed with ovarian cancer and 15,310 will succumb to the disease [1]. Ovarian cancer is a devastating illness in which only 20% of patients are diagnosed with stage I disease [2]. The poor prognosis associated with ovarian cancer is multifactorial; a lack of minimally invasive, early detection tests, subtle symptom development and tumor chemo-resistance. Even with the advent of chemo-resistance assays it is still difficult to predict drug resistance and only 10-15% of patients will remain in prolonged remission after initial cytotoxic therapy.

While annual pelvic examination is widely practiced, it lacks the sensitivity to be used a screening strategy for ovarian cancer [3]. Women at high risk for ovarian cancer may typically undergo screening with trans-vaginal ultrasound and serum CA-125. CA-125, however, remains a poor marker for early stage disease with a documented sensitivity of 40% [4,5]. Additionally, it has been shown that even in a high-risk, screened population, incident cases are still more likely to be advanced stage [6]. The identification of biomarkers that may assist in treatment planning and prediction of chemotherapy outcomes is highly desirable in this population of patients.

There is emerging research about the role of microRNAs in a variety of pathologic conditions; including both solid and hematologic malignancies. MicroRNAs (miRNAs) are small, 22-25 nucleotide non-coding sequences of RNA. These sequences control gene expression either by translational repression or degradation of the messenger RNA transcript after targeting the 3'UTR. Early studies with *Caenorhabditis elegans* showed that a great number of these sequences are highly conserved across all species, demonstrating the important roles that miRNAs play in cellular differentiation, proliferation and cell cycle control [7]. It is now recognized that miRNAs are frequently de-regulated in malignancy. Under-expressed miRNAs such as let-7 in lung cancer and mirs-15/16 in leukemia, are tumor suppressor genes, suppressing Ras and BCL2 respectively [8,9]. Over-expressed miRNAs such as mir-21 and the cluster miR-17-92, are oncogenes (oncomirs), targeting tumor suppressors PTEN and E2F1 in solid and hematologic malignancies respectively [10,11]. While miRNA research in gynecologic malignancies is in its infancy, the miRNA signature profile of ovarian cancer has recently been published [12-14].

The diagnostic and prognostic utility of circulating RNAs in both benign and malignant conditions has recently been revealed. Placental-associated circulating miRNAs correlate with pregnancy progression [15]. In malignant states, circulating mRNAs in renal cell carcinoma patients [16], as well as miRNAs from the serum of patients with diffuse large B cell lymphoma [17], have been shown to be stable and highly predictive of malignancy as well as survival. Recently, it has been demonstrated that the miRNA signature of circulating tumor exosomes of ovarian cancer patients demonstrates high correlation with miRNA expression of the primary tumor [18]. Ovarian cancer remains a disease for which improved non-invasive, serum screening tests are highly desirable.

In spite of considerable research into therapies to treat these diseases, they remain difficult to diagnose and treat effectively, and the mortality observed in patients indicates that improvements are needed in the diagnosis, treatment and prevention of ovarian cancer.

SUMMARY

In a first broad aspect, there is provided herein, a method of diagnosing whether a subject has, or is at risk for developing a ovarian-related disorder, determining a prognosis of a subject with ovarian related disorder, and/or treating a ovarian related disorder in a subject who has the ovarian related disorder, comprising: measuring the level of at least one biomarker in a test sample of serum from the subject, wherein an alteration in the level of the biomarker in the test sample, relative to the level of a corresponding biomarker in a control sample, is indicative of the subject either having, or being at risk for developing, the disorder.

In certain embodiments, the at least one biomarker differentially expressed between tumor tissue and non-tumor tissue, and is one or more of miR-21, miR92, miR-93, miR-126, miR-29a, miR-155, miR-127 and miR-99b, or functional variants thereof.

In certain embodiments, the level of the biomarker in the test sample is greater than the level of the corresponding biomarker in the control sample.

In certain embodiments, the biomarker is differentially expressed between tumor tissue and non-tumor tissue, and is one or more of miR-21, miR92, miR-93, miR-126 and miR-29a, or functional variants thereof.

In certain embodiments, the biomarker is differentially expressed between tumor tissue and non-tumor tissue, and is one or more of miR-21, miR92 and miR-93, or functional variants thereof.

In certain embodiments, the level of the at least one biomarker in the test sample is less than the level of the corresponding biomarker in the control sample. In certain embodiments, the biomarker is differentially expressed between tumor tissue and non-tumor tissue, and is one or more of miR-155, miR-127 and miR-99b, or functional variants thereof.

In another broad aspect, there is provided herein, a method of screening for one or more biomarkers for ovarian cancer in a subject, comprising: obtaining a sample of serum from the subject, conducting quantitative real-time polymerase chain reaction (RT-PCR), and quantifying one or more one biomarkers differentially expressed between tumor tissue and non-tumor tissue, wherein the biomarkers are selected from one or more of miR-21, miR92, miR-93, miR-126, miR-29a, miR-155, miR-127 and miR-99b, or functional variants thereof. In certain embodiments, the sample comprises a blood sample.

In certain embodiments, the sample comprises one or more of serum or plasma blood samples.

In another broad aspect, there is provided herein, a method biomarker for ovarian cancer, comprising at least one biomarker differentially expressed between tumor tissue and non-tumor tissue, wherein the biomarkers are selected from one or more of miR-21, miR92, miR-93, miR-126, miR-29a, miR-155, miR-127 and miR-99b, or functional variants thereof.

In another broad aspect, there is provided herein, a method distinct microRNA expression signature in ovarian tumors comprising alterations in the expression of one or more biomarkers that regulate tumor microRNA processing, wherein the biomarkers are selected from one or more of miR-21, miR92, miR-93, miR-126, miR-29a, miR-155, miR-127 and miR-99b, or functional variants thereof.

In another broad aspect, there is provided herein, a method for influencing transcript abundance and/or protein expression of target mRNAs in the ovary of a subject in need thereof, comprising deregulating one or more microRNAs selected from one or more of miR-21, miR92, miR-93, miR-126, miR-29a, miR-155, miR-127 and miR-99b, or functional variants thereof.

In certain embodiments, the method further includes inhibiting protein expression of cancer-related genes.

In certain embodiments, the method includes altering expression of one or more of miR-21, miR-92, mir-93, miR-126 and miR-129a to inhibit the protein expression of cancer-related genes.

In another broad aspect, there is provided herein, use of a large-scale gene expression profiling of microRNAs and/or protein-encoding RNAs to identify alterations in microRNA function that occur in human ovarian tumors.

In another broad aspect, there is provided herein, a method for screening for ovarian in a subject in need thereof, comprising the step of performing real-time polymerase chain reaction (RT-PCR) on a serum sample from the subject.

In another broad aspect, there is provided herein, a tumor gene signature for an ovarian related disorder comprising: one or more of: miR-21, miR92, miR-93, miR-126, miR-29a, miR-155, miR-127 and miR-99b, or functional variants thereof.

In another broad aspect, there is provided herein, a tumor gene signature for an ovarian related disorder comprising: one or more of: miR-21, miR92, miR-93, miR-126 and miR-29a, or functional variants thereof that are up-regulated; and, miR-155, miR-127 and miR-99b, or functional variants thereof, that are down regulated.

In another broad aspect, there is provided herein, a tumor gene signature for an ovarian related disorder comprising: one or more of: miR-21, miR92 and miR-93, or functional variants thereof.

In certain embodiments, the biomarker comprises host gene expression in ovarian tumors that are increased in ovarian tumors. In certain embodiments, the biomarkers include one or more of: miR-21, miR92, miR-93, miR-126 and miR-29a, or functional variants thereof.

In another broad aspect, there is provided herein, use of miR-21, miR92 and/or miR-93, or functional variants thereof, as a target for at least one gene in ovarian cancer cells and/or use in inhibiting protein expression of such gene.

In another broad aspect, there is provided herein, a method for regulating one or more of genes expressed by ovarian cancer cells, comprising the step of altering expression of miR-21, miR92 and/or miR-93 in ovarian cancer cells.

In another broad aspect, there is provided herein, use of binding of microRNAs to 3'UTR sequences to lead to degradation and/or accumulation of targeted mRNA in mammalian ovarian cancer cells.

In another broad aspect, there is provided herein, use of an inverse and/or a positive correlation between a microRNA and a mRNA in a human tissue predictive of a microRNA target gene for ovarian cancer.

In another broad aspect, there is provided herein, a miR-expression inhibitor comprising one or more of: miR-21, miR92, miR-93, miR-126 and miR-29a, or functional variants thereof.

In another broad aspect, there is provided herein, a miR-expression inhibitor comprising one or more of: miR-21, miR92 and/or miR-93, or functional variants thereof.

In another broad aspect, there is provided herein, a miR-expression antisense inhibitor comprising one or more of: miR-155, miR-127 and miR-99b, or functional variants thereof.

In another broad aspect, there is provided herein, an oncomiR biomarker of an ovarian disorder or disease, comprising one or more of: miR-21, miR92, miR-93, miR-126, miR-29a, miR-155, miR-127 and miR-99b, or functional variants thereof.

In another broad aspect, there is provided herein, an oncomiR biomarker of an ovarian disorder or disease, comprising one or more of: miR-21, miR92 and miR-93, or functional variants thereof.

In another broad aspect, there is provided herein, a method for regulating protein expression in ovarian cancer cells, comprising modulating the expression of one or more of: miR-21, miR92, miR-93, miR-126, miR-29a, miR-155, miR-127 and miR-99b, or functional variants thereof, in the ovarian cancer cells.

In another broad aspect, there is provided herein, a method for regulating protein expression in ovarian cancer cells, comprising modulating the expression of one or more of: miR-21, miR92 and miR-93, or functional variants thereof, in the ovarian cancer cells.

In another broad aspect, there is provided herein, a composition for repressing expression of one or more of genes in ovarian cancer cells, the composition comprising one or more of: miR-21, miR92, miR-93, miR-126, miR-29a, miR-155, miR-127 and miR-99b, or functional variants thereof.

In another broad aspect, there is provided herein, a composition for repressing expression of one or more of genes in ovarian cancer cells, the composition comprising one or more of: miR-21, miR92 and miR-93, or functional variants thereof.

In another broad aspect, there is provided herein, a method for regulating one or more of protein levels in a subject with ovarian cancer, comprising using one or more of: miR-21, miR92, miR-93, miR-126, miR-29a, miR-155, miR-127 and miR-99b, or functional variants thereof.

In another broad aspect, there is provided herein, a method for regulating one or more of protein levels in a subject with ovarian cancer, comprising using one or more of: miR-21, miR92 and miR-93, or functional variants thereof.

In another broad aspect, there is provided herein, a method for determining the prognosis of a subject with ovarian cancer, comprising measuring the level of at least one biomarker in a test sample of serum from the subject, wherein the biomarker is selected from one or more of miR-21, miR92, miR-93, miR-126, miR-29a, miR-155, miR-127 and miR-99b, or functional variants thereof, and wherein: i) the biomarker is associated with an adverse prognosis in ovarian cancer; and ii) an alteration in the level of the at least one biomarker in the test sample, relative to the level of a corresponding biomarker in a control sample, is indicative of an adverse prognosis.

In another broad aspect, there is provided herein, a method of diagnosing whether a subject has, or is at risk for developing, ovarian cancer, comprising: reverse transcribing RNA from a test sample of serum obtained from the subject to provide a set of target oligodeoxynucleotides; hybridizing the target oligodeoxynucleotides to a microarray comprising miRNA-specific probe oligonucleotides to provide a hybridization profile for the test sample; and comparing the test sample hybridization profile to a hybridization profile generated from a control sample, wherein an alteration in the signal of at least one miRNA is indicative of the subject either having, or being at risk for developing, ovarian cancer.

In certain embodiments, the signal of at least one miRNA, relative to the signal generated from the control sample, is down-regulated, and/or wherein the signal of at least one miRNA, relative to the signal generated from the control sample, is up-regulated.

In certain embodiments, an alteration in the signal of at least one biomarker miR-21, miR92, miR-93, miR-126, miR-29a, miR-155, miR-127 and miR-99b, or functional variants thereof are indicative of the subject either having, or being at risk for developing, an ovarian cancer with an adverse prognosis.

In another broad aspect, there is provided herein, a method of treating ovarian cancer in a subject who has an ovarian cancer in which at least one biomarker is down-regulated or up-regulated in the cancer cells of the subject relative to control cells, comprising: when the at least one biomarker is down-regulated in the cancer cells, administering to the subject an effective amount of at least one isolated biomarker, or an isolated variant or biologically-active fragment thereof, such that proliferation of cancer cells in the subject is inhibited; or when the at least one biomarker is up-regulated in the cancer cells, administering to the subject an effective amount of at least one compound for inhibiting expression of the at least one biomarker, such that proliferation of cancer cells in the subject is inhibited; wherein the biomarker is selected from one or more of miR-21, miR92, miR-93, miR-126, miR-29a, miR-155, miR-127 and miR-99b, or functional variants thereof.

In another broad aspect, there is provided herein, a method of treating ovarian cancer in a subject, comprising: determining the amount of at least one biomarker in ovarian cancer cells, relative to control cells; and altering the amount of biomarker expressed in the ovarian cancer cells by: administering to the subject an effective amount of at least one isolated biomarker, if the amount of the biomarker expressed in the cancer cells is less than the amount of the biomarker expressed in control cells; or administering to the subject an effective amount of at least one compound for inhibiting expression of the at least one biomarker, if the amount of the biomarker expressed in the cancer cells is greater than the amount of the biomarker expressed in control cells; wherein the biomarker is selected from one or more of miR-21, miR92, miR-93, miR-126, miR-29a, miR-155, miR-127 and miR-99b, or functional variants thereof.

In another broad aspect, there is provided herein, a pharmaceutical composition for treating ovarian cancer, comprising at least one isolated biomarker, and a pharmaceutically-acceptable carrier, wherein the biomarker is selected from one or more of miR-21, miR92, miR-93, miR-126, miR-29a, miR-155, miR-127 and miR-99b, or functional variants thereof. In certain embodiments, the biomarker corresponds to a biomarker that is up-regulated in ovarian cancer cells relative to control cells. In certain embodiments, the pharmaceutical composition comprises at least one miR expression-inhibitor compound and a pharmaceutically-acceptable carrier.

In another broad aspect, there is provided herein, a method of identifying an anti-ovarian cancer agent, comprising providing a test agent to a cell and measuring the level of at least one biomarker associated with increased expression levels in ovarian cancer cells, wherein a decrease in the level of the biomarker in the cell, relative to a control cell, is indicative of the test agent being an anti-ovarian cancer agent; and wherein the biomarker is selected from one or more of miR-21, miR92, miR-93, miR-126 and miR-29a, or functional variants thereof.

In another broad aspect, there is provided herein, a method of identifying an anti-ovarian cancer agent, comprising providing a test agent to a cell and measuring the level of at least one biomarker associated with decreased expression levels in ovarian cancer cells, wherein an increase in the level of the biomarker in the cell, relative to a control cell, is indicative of the test agent being an anti-ovarian cancer agent; and wherein the biomarker is selected from one or more of miR-155, miR-127 and miR-99b, or functional variants thereof.

In another broad aspect, there is provided herein a method of assessing the effectiveness of a therapy to prevent, diagnose and/or treat an ovarian cancer associated disease, comprising: subjecting an animal to a therapy whose effectiveness is being assessed, and determining the level of effectiveness of the treatment being tested in treating or preventing the disease, by evaluating at least one biomarker selected from one or more of: miR-21, miR92, miR-93, miR-126, miR-29a, miR-155, miR-127 and miR-99b, or functional variants thereof.

In certain embodiments, the candidate therapeutic agent comprises one or more of: pharmaceutical compositions, nutraceutical compositions, and homeopathic compositions.

In certain embodiments, the therapy being assessed is for use in a human subject.

In another broad aspect, there is provided herein, an article of manufacture comprising: at least one capture reagent that binds to a marker for an ovarian cancer associated disease comprising at least one biomarker selected from one or more of: miR-21, miR92, miR-93, miR-126, miR-29a, miR-155, miR-127 and miR-99b, or functional variants thereof.

In another broad aspect, there is provided herein, a kit for screening for a candidate compound for a therapeutic agent to treat a ovarian cancer associated disease, wherein the kit comprises: one or more reagents of at least one biomarker selected from one or more of: miR-21, miR92, miR-93, miR-126, miR-29a, miR-155, miR-127 and miR-99b, or functional variants thereof, and a cell expressing at least one biomarker. In certain embodiments, the presence of the biomarker is detected using a reagent comprising an antibody or an antibody fragment which specifically binds with at least one biomarker.

In another broad aspect, there is provided herein, use of an agent that interferes with an ovarian cancer associated disease response signaling pathway, for the manufacture of a medicament for treating, preventing, reversing or limiting the severity of the disease complication in an individual, wherein the agent comprises at least one biomarker selected from one or more of: miR-21, miR92, miR-93, miR-126, miR-29a, miR-155, miR-127 and miR-99b, or functional variants thereof.

In another broad aspect, there is provided herein, a method of treating, preventing, reversing or limiting the severity of an ovarian cancer associated disease complication in an individual in need thereof, comprising: administering to the individual an agent that interferes with at least an ovarian cancer associated disease response cascade, wherein the agent comprises at least one biomarker selected from one or more of: miR-21, miR92, miR-93, miR-126, miR-29a, miR-155, miR-127 and miR-99b, or functional variants thereof.

In another broad aspect, there is provided herein, use of an agent that interferes with at least an ovarian cancer associated disease response cascade, for the manufacture of a medicament for treating, preventing, reversing or limiting the severity of an ovarian cancer-related disease complication in an individual, wherein the agent comprises at least one biomarker selected from one or more of: miR-21, miR92, miR-93, miR-126, miR-29a, miR-155, miR-127 and miR-99b, or functional variants thereof.

In another broad aspect, there is provided herein, a composition comprising an inhibitor of one or more of miR-21, miR-92 and miR-93.

In another broad aspect, there is provided herein, a method of treating an ovarian disorder in a subject in need thereof, comprising administering to a subject a therapeutically effective amount of the composition. In certain embodiments, the composition is administered prophylactically. In certain embodiments, administration of the composition delays the onset of one or more symptoms of the disorder.

In certain embodiments, administration of the peptide inhibits development of ovarian cancer.

In certain embodiments, administration of the peptide inhibits tumor growth.

In another broad aspect, there is provided herein, a method for detecting the presence of an ovarian cancer in a biological sample, the method comprising: exposing the biological sample suspected of containing ovarian cancer to a marker therefor; and detecting the presence or absence of the marker, if any, in the sample; wherein the biomarker is selected from one or more of miR-21, miR92, miR-93, miR-126, miR-29a, miR-155, miR-127 and miR-99b, or functional variants thereof. In certain embodiments, the marker includes a detectable label.

In certain embodiments, the method further comprising comparing the amount of the marker in the biological sample from the subject to an amount of the marker in a corresponding biological sample from a normal subject. In certain embodiments, the method further comprises collecting a plurality of biological samples from a subject at different time points and comparing the amount of the marker in each biological sample to determine if the amount of the marker is increasing or decreasing in the subject over time.

In another broad aspect, there is provided herein, a method for treating an ovarian cancer in a subject, the method comprising: administering to the subject in need thereof a therapeutically effective amount of an ovarian receptor agonist comprising: an inhibitor of one or more of: miR-21, miR92, miR-93, miR-126 and miR-29a, or functional variants thereof.

In another broad aspect, there is provided herein, a method for treating an ovarian cancer in a subject, the method comprising: administering to the subject in need thereof a therapeutically effective amount of an ovarian receptor agonist comprising: an antisense inhibitor of one or more of: miR-155, miR-127 and miR-99b, or functional variants thereof.

In another broad aspect, there is provided herein, a use, to manufacture a drug for the treatment of an ovarian cancer, comprised of a nucleic acid molecule chosen from one or more of: miR-21, miR92, miR-93, miR-126, miR-29a, miR-155, miR-127 and miR-99b, or functional variants thereof. In certain embodiments, the drug comprises a nucleic acid molecule presenting a sequence chosen from one or more of: miR-21, miR92, miR-93, miR-126, miR-29a, miR-155, miR-127 and miR-99b, or functional variants thereof.

In another broad aspect, there is provided herein, an in vitro method to identify effective therapeutic agents or combinations of therapeutic agents to induce the differentiation of ovarian cancer cells, the method comprising the stages of: i) culturing of cells derived from an ovarian tumor, ii) adding at least one compound to the culture medium of the cell line, iii) analyzing the evolution of the level of expression of at least one miR between stages (i) and (ii), and iv) identifying compounds or combinations of compounds inducing a change in the level of expression of the miR between stages (i) and (ii). In certain embodiments, stage (iii) includes the analysis of the level of expression of at least one miR. In certain embodiments, stage (iv) includes the identification of the compounds or combinations of compounds modulating the level of expression of at least one miR. In certain embodiments, stage (iv) includes the identification of compounds or combinations of compounds reducing the level of expression of at least one miR. In certain embodiments, the compound is a therapeutic agent for the treatment of cancer.

In another broad aspect, there is provided herein, a method for classifying an ovarian tissue from a subject comprising: measuring the expression of one or more of: miR-21, miR92, miR-93, miR-126, miR-29a, miR-155, miR-127 and miR-99b, or functional variants thereof, among the miR in a test cell population, wherein at least one cell in the test cell population is capable of expressing one or more of: miR-21, miR92, miR-93, miR-126, miR-29a, miR-155, miR-127 and miR-99b, or functional variants thereof among the miR; comparing the expression of the miR(s) to the expression of the miR(s) in a reference cell population comprising at least one cell for which an ovarian cancer classification is known; and identifying a difference, if present, in expression levels of one or more miR(s) in the test cell population and reference cell population, thereby classifying the ovarian cancer in the subject.

In certain embodiments, a difference in the expression in the test cell population as compared to the reference cell population indicates that the test cell population has a different classification as the cells from the reference cell population.

In certain embodiments, a similar expression pattern in the test cell population as compared to the reference cell population indicates that the test cell population has the same classification as the cells from the reference cell population.

In certain embodiments, the reference cell population is a plurality of cells or a database. In certain embodiments, the reference cell population is selected from the group consisting of: a reference cell population classified as a cell population from normal ovarian tissue, a reference cell population classified as a cell population from benign ovarian tissue and a reference cell population classified as a cell population from malignant ovarian tissue.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

DETAILED DESCRIPTION OF THE INVENTION

Figure 1:
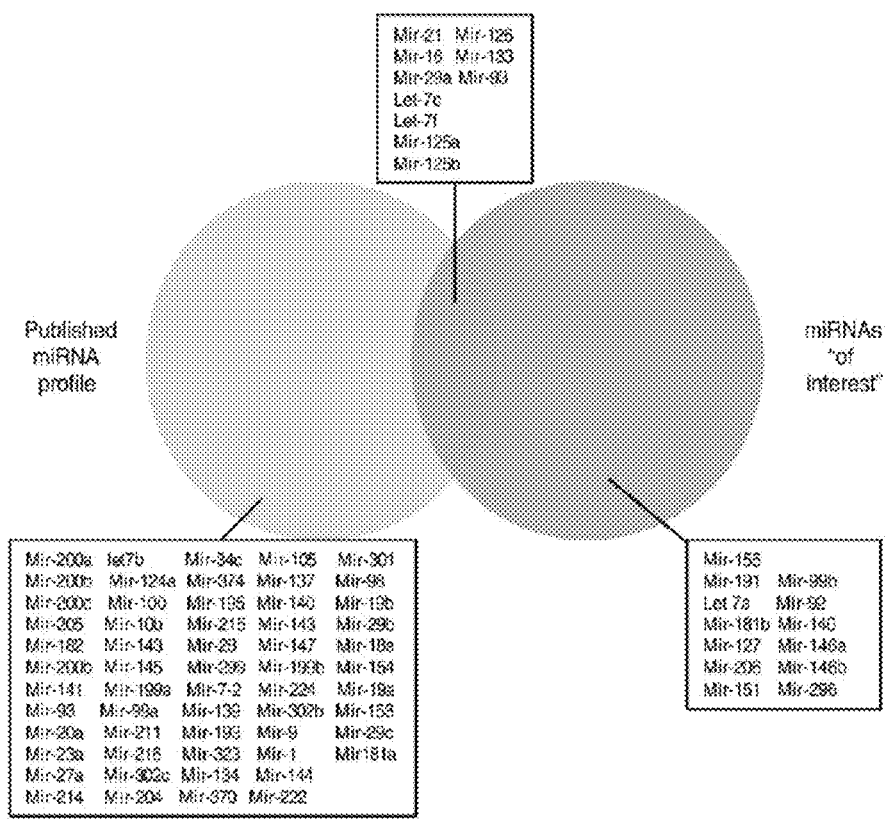
FIG. 1: Comparison of published miRNA profile and differentially expressed miRNAs from ovarian cancer patient serum.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

MicroRNAs are small non-coding RNAs that regulate the expression of protein-coding genes. MicroRNA expression becomes altered with the development and progression of ovarian cancer. Some of these microRNAs regulate the expression of cancer-related genes in ovarian cancer cells. As used herein interchangeably, a "miR gene product," "microRNA," "miR," or "miRNA" refers to the unprocessed or processed RNA transcript from a miR gene.

As used herein, "biomarker" can include one or more of a "miR gene product," "microRNA," "miR," or "miRNA," or a protein-encoding RNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

The present invention encompasses methods of diagnosing whether a subject has, or is at risk for developing, an ovarian related disorder. As used herein, a "subject" can be any mammal that has, or is suspected of having, ovarian cancer.

We offer a description of miRNA extraction from the serum of ovarian cancer patients, the differential expression of a number of these miRNAs between patients and healthy controls as well as a novel real-time PCR microarray detection method.

The present invention is further explained in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference.

EXAMPLE I

Methods

Following approval from the Institutional Review Board of The Ohio State University College of Medicine we analyzed serum samples from 28 patients with newly diagnosed ovarian cancer and 15 normal controls. These serum samples were collected at the time of initial consultation, prior to definitive surgical management and/or adjuvant therapy. The serum was obtained as part of a prospective tissue and serum procurement study and was stored at −80° C. Fresh serum was obtained from 15 healthy women who volunteered to serve as controls. The frozen serum was thawed and RNA was extracted from the patient and control populations simultaneously. None of the healthy controls had previously been diagnosed with a malignancy.

RNA was extracted from 250 µl of serum using the Tri-Reagent BD (Molecular Research Center, Inc., Cincinnati, Ohio) as described by the manufacturer. RNA quality was assessed with the ThermoScientific NanoDrop1000 (Thermo Fisher Scientific, Inc., Waltham, Mass.). MicroRNA expression profiling was performed with RNA from 4 controls and 9 cancer patients utilizing the TaqMan Array Human MicroRNA Panel (v. 1, Applied Biosystems, Foster City, Calif.) using 50 ng of RNA per port for a total of 400 ng. This array contains 365 miRNA targets as well as endogenous controls. Normalization was performed with the small nuclear RNAs (snRNAs) U44 and U48. These snRNAs are stably expressed reference genes suitable for use as normalizers in TaqMan assays.

In addition to identifying differentially expressed miRNAs on the microarray panel, a second goal was to identify miRNAs that may serve as normalizers given the lack of published data on the subject. Twenty-one miRNAs from the expression profile were empirically chosen for further examination in control and patient serum (11 controls and 19 patients). These were chosen based on apparent Ct differences of 4 cycles or greater between controls and patients. Two miRNAs (142-3p and 16) were identified as potential normalizers given consistent expression across all patient and control samples. For the miRNAs of interest the single tube TaqMan MicroRNA Assays were used. All reagents, primers and probes were obtained from Applied Biosystems (Applied Biosystems, Foster City, Calif.). One nanogram of RNA per sample was used for the assays. MiRNA-142-3p was used as a normalizer All RT reactions, including no-template (no cDNA) controls and minus controls (no reverse transcriptase), were run in a GeneAmp PCR 9700 Thermocycler (Applied Biosystems). Gene expression levels were quantified using the ABI Prism 7900HT Sequence detection system (Applied Biosystems). Comparative real-time PCR was performed in triplicate, including no-template controls.

Expression of the microRNAs was calculated utilizing the comparative Ct. method. Statistical analysis was performed with STATA v. 10 (College Station, Tex.). Expression was compared using the Mann-Whitney test. P-values >0.05 were considered statistically significant.

Results

Twenty-eight patients with epithelial ovarian cancer were included in this study. Stage breakdown was as follows: stage 18 (28.5%), stage II-2 (7.1%), stage III-8 (28.5%) stage IV-10 (35.7%). Histologic breakdown was as follows: serous (60%), clear cell (21.2%), endometrioid (12%), mucinous (6%). Median age was 57 years (age range 34-79). Similar to most groups with ovarian cancer, the majority (66%) had stage III or IV disease, and was predominately (60%) serous histology.

Primary miRNA expression profiling with microarray identified 23 miRNAs (including 2 normalizers) of interest. We created a Venn diagram in order to compare the 23 miRNAs of interest from our initial test set with known miRNA signature profiles. There were 10 miRNAs of interest in such group that were in common with miRNAs that have been published in the literature as part of the miRNA signatures of ovarian cancer (FIG. 1).

Figure 2:
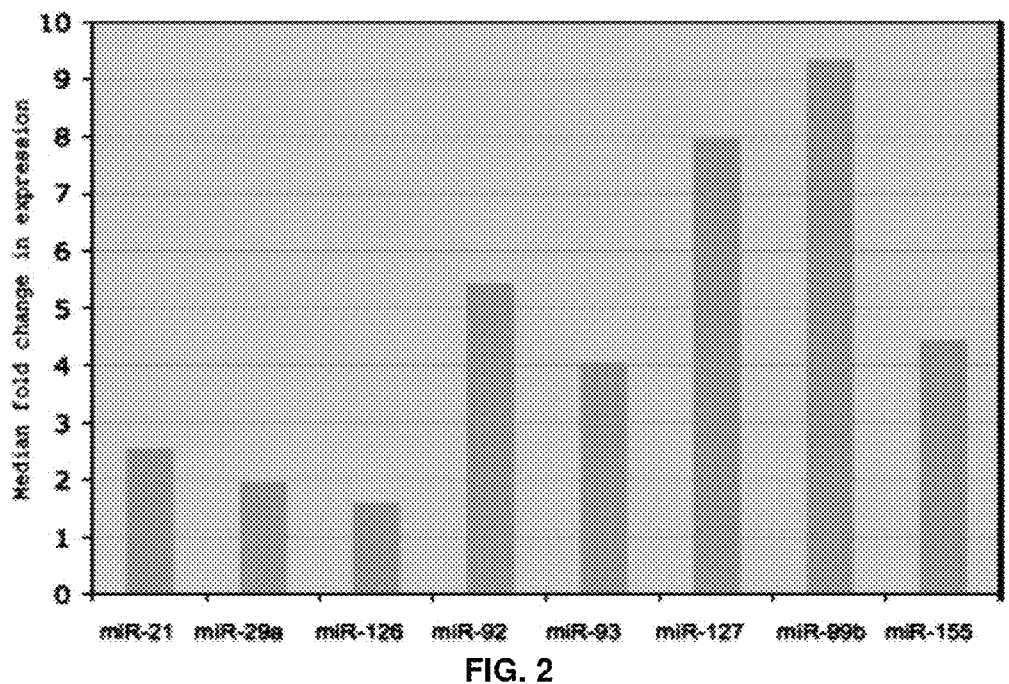
FIG. 2: Median fold-change differences in differentially expressed miRNAs between patient and control serum.

On follow up quantitative RT-PCR of the 21 miRNAs, 5 miRNAs were over-expressed (miRNAs-21, 29a, 92, 93 and 126, p=0.0002, p=0.003, p=0.0001, p=0.0003, p=0.007) and 3 miRNAs were under-expressed (mir-127, 155 and 99b, p=0.0001, p=0.0003, p=0.0001) in the serum of ovarian cancer patients compared to controls. Fold-differences in median expression of the miRNAs in patients versus controls are demonstrated in FIG. 2.

Three patients were identified with pre-operative CA-125<35 U/ml. We then examined the three miRNAs with the highest serum expression, miRs-21, 92 and 93 for expression patterns in those patients with normal CA-125 in order to determine if miRNA patterns mimicked CA-125 patterns. These three miRNAs were found to be significantly over-expressed in these patients when median expression in the patient population was compared to controls (Table 1).

TABLE 1 miRNA over-expression in patients with normal pre-operative CA-125

| ID | FIGO Stage | CA-125 (u/ml) | miR-21 Patient [a]/ Control [b] | miR-92 Patient/ Control [c] | miR-93 Patient/ Control [d] |
|---|---|---|---|---|---|
| 1050133 | IIC | 34 | 1.89/.79 | 27.5/4.3 | 2.37/.76 |
| 1050130 | IV | 13.4 | 1.54/.79 | 13.8/4.3 | 14/.76 |
| 1010026 | IA | 16.9 | 1.46/.79 | 16.1/4.3 | 3.5/.76 |

[a] Individual patient serum miRNA expression is defined as the 2(ΔCt).
[b] Inter-quartile range for median expression of miR-21 in controls: (.68-.93).
[c] Inter-quartile range for median expression of miR-92 in controls: (2.9-8.7).
[d] Inter-quartile range for median expression of miR-93 in controls: (.36-1.3).

There was no correlation between miRNA status and grade, stage or histologic subtype. Due to the small sample size and recent diagnosis of disease we did not attempt to correlate miRNA status with progression-free interval or survival.

Discussion

We demonstrate that the extraction of RNA and identification of miRNAs from the serum of individuals diagnosed with ovarian cancer is practicable.

The inventors herein show herein the first description of using a real-time PCR, microarray platform to screen large numbers of miRNAs while minimizing the amount of RNA needed.

Additionally, the inventors herein show that miRNAs can as early detection biomarkers in patients with normal CA-125.

A profile was created that was subsequently examined on a set of 19 patients and 11 healthy controls. Out of the 21 miRNAs of interest that we selected, 10 miRNAs were common to published ovarian cancer profiles. Among the 5 over-expressed miRNAs that we discovered are three potential oncomirs; miRs-21, 92 and 93. Over-expression of miR-21 has been demonstrated in glioblastoma, breast, colon, prostate, lung, pancreas and stomach cancers [19,20]. It has been shown to modulate expression of PTEN in hepatocellular carcinoma [10] as well as PDCD4 and maspin, two genes involved in regulating invasion and metastasis [21,22].

The most consistently over-expressed miRNA in serum from patients was miR-92. Mir-92a-1 is part of the mir-17-92 polycistron, located on chromosome 13q13. A known oncomir, mir-17-92-enforced expression in a transgenic mouse model of lymphoma unequivocally demonstrated accelerated lymphoma progression [23]. Over-expression of miR-93 was associated with decreased progression-free and overall survival in ovarian cancer patients [13]. In gastric tumors, this cluster negatively regulated TGFβ tumor suppressor activities [24]. The proposed oncogenic activities of both miR-92 and miR-93 agree with our serum findings.

Contrary to the published ovarian cancer profiles, the inventors herein now have demonstrated significant over-expression of miR-29a and miR-126 in the sera from ovarian cancer patients. There have been a number of tumor suppressor activities proposed for both miR-126 and 29a. Mir-126 has been implicated as a "metastatic-suppressor" in breast cancer with loss associated with poor outcome [25]. Mir-29a has been found to be under-expressed in lung cancers; having been implicated in the modulation of methylation patterns seen in lung cancer [26]. While over expression of these miRNAs would tend to suggest they behave as oncomirs, TargetScan (4.2) does predict PTEN as a potential target of miR-29a.

Mir-127 has been identified as one of thirty-one down-regulated miRNAs in ovarian cancer cell lines [14]. It has recently been shown to be embedded in a CpG island and silenced completely in most cancer cell lines. In this same study, it was demonstrated that treatment of cell lines with 5-aza-2' deoxycytidine not only restored miR-127 expression but also reduced expression of the proto-oncogene BCL6 [27]. Taken together these results identify miR-127 as a tumor suppressor gene, supporting our findings of decreased expression in patient serum.

It is to be noted that there is a limited amount of published data regarding the extraction of quality miRNA from serum. Despite experiencing RNA degradation as well as genomic DNA contamination (results not shown), the inventors found that only 400 ng of total RNA are required for the TaqMan Array Human MicroRNA. Additionally, given that the amplicons of interest are approximately 25-30 nucleotides, the inventors determined that some degradation of the RNA is tolerable.

Also, the inventors herein have also determined that the controls used in real-time PCR account for both cross contamination by reagents (no template control) as well as genomic DNA contamination (RT minus control).

Since the microarray chips typically only utilize up to about 5 μg of sample, the real-time based method described herein does not require extracting large amounts of pure RNA from serum. The inventors herein show for the first time that a real-time PCT method can be to obtain a miRNA profile on serum RNA.

Examples of Uses and Definitions Thereof

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., Handbook of Experimental Immunology, Vols. I-IV (D. M. Weir and C. C. Blackwell eds., Blackwell Scientific Publications); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.).

As such, the definitions herein are provided for further explanation and are not to be construed as limiting.

The articles "a" and "an" are used herein to refer to one or to more than one (i.e., to at least one) of the grammatical object of the article. By way of example, "an element" means one element or more than one element.

A "marker" and "biomarker" is a gene and/or protein and/or functional variants thereof whose altered level of expression in a tissue or cell from its expression level in normal or healthy tissue or cell is associated with a disorder and/or disease state.

The "normal" level of expression of a marker is the level of expression of the marker in cells of a human subject or patient not afflicted with a disorder and/or disease state.

An "over-expression" or "significantly higher level of expression" of a marker refers to an expression level in a test sample that is greater than the standard error of the assay employed to assess expression, and in certain embodiments, at least twice, and in other embodiments, three, four, five or ten times the expression level of the marker in a control sample (e.g., sample from a healthy subject not having the marker associated disorder and/or disease state) and in certain embodiments, the average expression level of the marker in several control samples.

A "significantly lower level of expression" of a marker refers to an expression level in a test sample that is at least twice, and in certain embodiments, three, four, five or ten times lower than the expression level of the marker in a control sample (e.g., sample from a healthy subject not having the marker associated disorder and/or disease state) and in certain embodiments, the average expression level of the marker in several control samples.

A kit is any manufacture (e.g. a package or container) comprising at least one reagent, e.g., a probe, for specifically detecting the expression of a marker. The kit may be promoted, distributed or sold as a unit for performing the methods of the present invention.

"Proteins" encompass marker proteins and their fragments; variant marker proteins and their fragments; peptides and polypeptides comprising an at least 15 amino acid segment of a marker or variant marker protein; and fusion proteins comprising a marker or variant marker protein, or an at least 15 amino acid segment of a marker or variant marker protein.

The compositions, kits and methods described herein have the following non-limiting uses, among others:

1) assessing whether a subject is afflicted with a disorder and/or disease state;
2) assessing the stage of a disorder and/or disease state in a subject;
3) assessing the grade of a disorder and/or disease state in a subject;
4) assessing the nature of a disorder and/or disease state in a subject;
5) assessing the potential to develop a disorder and/or disease state in a subject;
6) assessing the histological type of cells associated with a disorder and/or disease state in a subject;
7) making antibodies, antibody fragments or antibody derivatives that are useful for treating a disorder and/or disease state in a subject;
8) assessing the presence of a disorder and/or disease state in a subject's cells;
9) assessing the efficacy of one or more test compounds for inhibiting a disorder and/or disease state in a subject;
10) assessing the efficacy of a therapy for inhibiting a disorder and/or disease state in a subject;
11) monitoring the progression of a disorder and/or disease state in a subject;
12) selecting a composition or therapy for inhibiting a disorder and/or disease state in a subject;
13) treating a subject afflicted with a disorder and/or disease state;
14) inhibiting a disorder and/or disease state in a subject;
15) assessing the harmful potential of a test compound; and
16) preventing the onset of a disorder and/or disease state in a subject at risk therefor.

Screening Methods

Animal models can be created to enable screening of therapeutic agents useful for treating or preventing a disorder and/or disease state in a subject. Accordingly, the methods are useful for identifying therapeutic agents for treating or preventing a disorder and/or disease state in a subject. The methods comprise administering a candidate agent to an animal model made by the methods described herein, and assessing at least one response in the animal model as compared to a control animal model to which the candidate agent has not been administered. If at least one response is reduced in symptoms or delayed in onset, the candidate agent is an agent for treating or preventing the disease.

The candidate agents may be pharmacologic agents already known in the art or may be agents previously unknown to have any pharmacological activity. The agents may be naturally arising or designed in the laboratory. They may be isolated from microorganisms, animals or plants, or may be produced recombinantly, or synthesized by any suitable chemical method. They may be small molecules, nucleic acids, proteins, peptides or peptidomimetics. In certain embodiments, candidate agents are small organic compounds having a molecular weight of more than 50 and less than about 2,500 Daltons. Candidate agents comprise functional groups necessary for structural interaction with proteins. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. There are, for example, numerous means available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. In certain embodiments, the candidate agents can be obtained using any of the numerous approaches in combinatorial library methods art, including, by non-limiting example: biological libraries; spatially addressable parallel solid phase or solution phase libraries; synthetic library methods requiring deconvolution; the "one-bead one-compound" library method; and synthetic library methods using affinity chromatography selection.

In certain further embodiments, certain pharmacological agents may be subjected to directed or random chemical modifications, such as acylation, alkylation, esterification, amidification, etc. to produce structural analogs.

The same methods for identifying therapeutic agents for treating a disorder and/or disease state in a subject can also be used to validate lead compounds/agents generated from in vitro studies.

The candidate agent may be an agent that up- or down-regulates one or more of a disorder and/or disease state in a subject response pathway. In certain embodiments, the candidate agent may be an antagonist that affects such pathway.

Methods for Treating a Disorder and/or Disease State

There is provided herein methods for treating, inhibiting, relieving or reversing a disorder and/or disease state response. In the methods described herein, an agent that interferes with a signaling cascade is administered to an individual in need thereof, such as, but not limited to, subjects in whom such complications are not yet evident and those who already have at least one such response.

In the former instance, such treatment is useful to prevent the occurrence of such response and/or reduce the extent to which they occur. In the latter instance, such treatment is useful to reduce the extent to which such response occurs, prevent their further development or reverse the response.

In certain embodiments, the agent that interferes with the response cascade may be an antibody specific for such response.

Expression of Biomarker(s)

Expression of a marker can be inhibited in a number of ways, including, by way of a non-limiting example, an antisense oligonucleotide can be provided to the disease cells in order to inhibit transcription, translation, or both, of the marker(s). Alternately, a polynucleotide encoding an antibody, an antibody derivative, or an antibody fragment which specifically binds a marker protein, and operably linked with an appropriate promoter/regulator region, can be provided to the cell in order to generate intracellular antibodies which will inhibit the function or activity of the protein. The expression and/or function of a marker may also be inhibited by treating the disease cell with an antibody, antibody derivative or antibody fragment that specifically binds a marker protein. Using the methods described herein, a variety of molecules, particularly including molecules sufficiently small that they are able to cross the cell membrane, can be screened in order to identify molecules which inhibit expression of a marker or inhibit the function of a marker protein. The compound so identified can be provided to the subject in order to inhibit disease cells of the subject.

Any marker or combination of markers, as well as any certain markers in combination with the markers, may be used in the compositions, kits and methods described herein. In general, it is desirable to use markers for which the difference between the level of expression of the marker in disease cells and the level of expression of the same marker in normal system cells is as great as possible. Although this difference can be as small as the limit of detection of the method for assessing expression of the marker, it is desirable that the difference be at least greater than the standard error of the assessment method, and, in certain embodiments, a difference of at least 2-, 3-, 4-, 5-, 6-, 7-, 8-, 9-, 10-, 15-, 20-, 100-, 500-, 1000-fold or greater than the level of expression of the same marker in normal tissue.

It is recognized that certain marker proteins are secreted to the extracellular space surrounding the cells. These markers are used in certain embodiments of the compositions, kits and methods, owing to the fact that such marker proteins can be detected in a body fluid sample, which may be more easily collected from a human subject than a tissue biopsy sample. In addition, in vivo techniques for detection of a marker protein include introducing into a subject a labeled antibody directed against the protein. For example, the antibody can be labeled with a radioactive marker whose presence and location in a subject can be detected by standard imaging techniques.

In order to determine whether any particular marker protein is a secreted protein, the marker protein is expressed in, for example, a mammalian cell, such as a human cell line, extracellular fluid is collected, and the presence or absence of the protein in the extracellular fluid is assessed (e.g. using a labeled antibody which binds specifically with the protein).

It will be appreciated that subject samples containing such cells may be used in the methods described herein. In these embodiments, the level of expression of the marker can be assessed by assessing the amount (e.g., absolute amount or concentration) of the marker in a sample. The cell sample can, of course, be subjected to a variety of post-collection preparative and storage techniques (e.g., nucleic acid and/or protein extraction, fixation, storage, freezing, ultrafiltration, concentration, evaporation, centrifugation, etc.) prior to assessing the amount of the marker in the sample.

It will also be appreciated that the markers may be shed from the cells into, for example, the respiratory system, digestive system, the blood stream and/or interstitial spaces. The shed markers can be tested, for example, by examining the sputum, BAL, serum, plasma, urine, stool, etc.

The compositions, kits and methods can be used to detect expression of marker proteins having at least one portion which is displayed on the surface of cells which express it. For example, immunological methods may be used to detect such proteins on whole cells, or computer-based sequence analysis methods may be used to predict the presence of at least one extracellular domain (i.e., including both secreted proteins and proteins having at least one cell-surface domain). Expression of a marker protein having at least one portion which is displayed on the surface of a cell which expresses it may be detected without necessarily lysing the cell (e.g., using a labeled antibody which binds specifically with a cell-surface domain of the protein).

Expression of a marker may be assessed by any of a wide variety of methods for detecting expression of a transcribed nucleic acid or protein. Non-limiting examples of such methods include immunological methods for detection of secreted, cell-surface, cytoplasmic or nuclear proteins, protein purification methods, protein function or activity assays, nucleic acid hybridization methods, nucleic acid reverse transcription methods and nucleic acid amplification methods.

In a particular embodiment, expression of a marker is assessed using an antibody (e.g., a radio-labeled, chromophore-labeled, fluorophore-labeled or enzyme-labeled antibody), an antibody derivative (e.g., an antibody conjugated with a substrate or with the protein or ligand of a protein-ligand pair), or an antibody fragment (e.g., a single-chain antibody, an isolated antibody hypervariable domain, etc.) which binds specifically with a marker protein or fragment thereof, including a marker protein which has undergone all or a portion of its normal post-translational modification.

In another particular embodiment, expression of a marker is assessed by preparing mRNA/cDNA (i.e., a transcribed polynucleotide) from cells in a subject sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide; preferably, it is not amplified. Expression of one or more markers can likewise be detected using quantitative PCR to assess the level of expression of the marker(s). Alternatively, any of the many methods of detecting mutations or variants (e.g., single nucleotide polymorphisms, deletions, etc.) of a marker may be used to detect occurrence of a marker in a subject.

In a related embodiment, a mixture of transcribed polynucleotides obtained from the sample is contacted with a substrate having fixed thereto a polynucleotide complementary to or homologous with at least a portion (e.g., at least 7, 10, 15, 20, 25, 30, 40, 50, 100, 500, or more nucleotide residues) of a marker nucleic acid. If polynucleotides complementary to or homologous with are differentially detectable on the substrate (e.g., detectable using different chromophores or fluorophores, or fixed to different selected positions), then the levels of expression of a plurality of markers can be assessed simultaneously using a single substrate (e.g., a "gene chip" microarray of polynucleotides fixed at selected positions). When a method of assessing marker expression is used which involves hybridization of one nucleic acid with another, it is desired that the hybridization be performed under stringent hybridization conditions.

In certain embodiments, the biomarker assays can be performed using mass spectrometry or surface plasmon resonance. In various embodiments, the method of identifying an agent active against a disorder and/or disease state in a subject can include one or more of: a) providing a sample of cells containing one or more markers or derivative thereof; b) preparing an extract from such cells; c) mixing the extract with a labeled nucleic acid probe containing a marker binding site; and, d) determining the formation of a complex between the marker and the nucleic acid probe in the presence or absence of the test agent. The determining step can include subjecting said extract/nucleic acid probe mixture to an electrophoretic mobility shift assay.

In certain embodiments, the determining step comprises an assay selected from an enzyme linked immunoabsorption assay (ELISA), fluorescence based assays and ultra high throughput assays, for example surface plasmon resonance (SPR) or fluorescence correlation spectroscopy (FCS) assays. In such embodiments, the SPR sensor is useful for direct real-time observation of biomolecular interactions since SPR is sensitive to minute refractive index changes at a metal-dielectric surface. SPR is a surface technique that is sensitive to changes of $10^5$ to $10^{-6}$ refractive index (RI) units within approximately 200 nm of the SPR sensor/sample interface. Thus, SPR spectroscopy is useful for monitoring the growth of thin organic films deposited on the sensing layer.

Because the compositions, kits, and methods rely on detection of a difference in expression levels of one or more markers, it is desired that the level of expression of the marker is significantly greater than the minimum detection limit of the method used to assess expression in at least one of normal cells and cancer-affected cells.

It is understood that by routine screening of additional subject samples using one or more of the markers, it will be realized that certain of the markers are over-expressed in cells of various types, including a specific disorder and/or disease state in a subject.

In addition, as a greater number of subject samples are assessed for expression of the markers and the outcomes of the individual subjects from whom the samples were obtained are correlated, it will also be confirmed that altered expression of certain of the markers are strongly correlated with a disorder and/or disease state in a subject and that altered expression of other markers are strongly correlated with other diseases. The compositions, kits, and methods are thus useful for characterizing one or more of the stage, grade, histological type, and nature of a disorder and/or disease state in a subject.

When the compositions, kits, and methods are used for characterizing one or more of the stage, grade, histological type, and nature of a disorder and/or disease state in a subject, it is desired that the marker or panel of markers is selected such that a positive result is obtained in at least about 20%, and in certain embodiments, at least about 40%, 60%, or 80%, and in substantially all subjects afflicted with a disorder and/or disease state of the corresponding stage, grade, histological type, or nature. The marker or panel of markers invention can be selected such that a positive predictive value of greater than about 10% is obtained for the general population (in a non-limiting example, coupled with an assay specificity greater than 80%).

When a plurality of markers are used in the compositions, kits, and methods, the level of expression of each marker in a subject sample can be compared with the normal level of expression of each of the plurality of markers in non-disorder and/or non-disease samples of the same type, either in a single reaction mixture (i.e. using reagents, such as different fluorescent probes, for each marker) or in individual reaction mixtures corresponding to one or more of the markers. In one embodiment, a significantly increased level of expression of more than one of the plurality of markers in the sample, relative to the corresponding normal levels, is an indication that the subject is afflicted with a disorder and/or disease state. When a plurality of markers is used, 2, 3, 4, 5, 8, 10, 12, 15, 20, 30, or 50 or more individual markers can be used; in certain embodiments, the use of fewer markers may be desired.

In order to maximize the sensitivity of the compositions, kits, and methods (i.e. by interference attributable to cells of system origin in a subject sample), it is desirable that the marker used therein be a marker which has a restricted tissue distribution, e.g., normally not expressed in a non-system tissue.

It is recognized that the compositions, kits, and methods will be of particular utility to subjects having an enhanced risk of developing a disorder and/or disease state in a subject and their medical advisors. Subjects recognized as having an enhanced risk of developing a disorder and/or disease include, for example, subjects having a familial history of such disorder or disease.

The level of expression of a marker in normal human system tissue can be assessed in a variety of ways. In one embodiment, this normal level of expression is assessed by assessing the level of expression of the marker in a portion of system cells which appear to be normal and by comparing this normal level of expression with the level of expression in a portion of the system cells which is suspected of being abnormal. Alternately, and particularly as further information becomes available as a result of routine performance of the methods described herein, population-average values for normal expression of the markers may be used. In other embodiments, the 'normal' level of expression of a marker may be determined by assessing expression of the marker in a subject sample obtained from a non-afflicted subject, from a subject sample obtained from a subject before the suspected onset of a disorder and/or disease state in the subject, from archived subject samples, and the like.

There is also provided herein compositions, kits, and methods for assessing the presence of disorder and/or disease state cells in a sample (e.g. an archived tissue sample or a sample obtained from a subject). These compositions, kits, and methods are substantially the same as those described above, except that, where necessary, the compositions, kits, and methods are adapted for use with samples other than subject samples. For example, when the sample to be used is a parafinized, archived human tissue sample, it can be necessary to adjust the ratio of compounds in the compositions, in the kits, or the methods used to assess levels of marker expression in the sample.

Kits and Reagents

The kits are useful for assessing the presence of disease cells (e.g. in a sample such as a subject sample). The kit comprises a plurality of reagents, each of which is capable of binding specifically with a marker nucleic acid or protein. Suitable reagents for binding with a marker protein include antibodies, antibody derivatives, antibody fragments, and the like. Suitable reagents for binding with a marker nucleic acid (e.g. a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kits may optionally comprise additional components useful for performing the methods described herein. By way of example, the kit may comprise fluids (e.g. SSC buffer) suitable for annealing complementary nucleic acids or for binding an antibody with a protein with which it specifically binds, one or more sample compartments, an instructional material which describes performance of the method, a sample of normal system cells, a sample of cancer-related disease cells, and the like.

Methods of Producing Antibodies

There is also provided herein a method of making an isolated hybridoma which produces an antibody useful for assessing whether a subject is afflicted with a disorder and/or disease state. In this method, a protein or peptide comprising the entirety or a segment of a marker protein is synthesized or isolated (e.g. by purification from a cell in which it is expressed or by transcription and translation of a nucleic acid encoding the protein or peptide in vivo or in vitro). A vertebrate, for example, a mammal such as a mouse, rat, rabbit, or sheep, is immunized using the protein or peptide. The vertebrate may optionally (and preferably) be immunized at least one additional time with the protein or peptide, so that the vertebrate exhibits a robust immune response to the protein or peptide. Splenocytes are isolated from the immunized vertebrate and fused with an immortalized cell line to form hybridomas, using any of a variety of methods. Hybridomas formed in this manner are then screened using standard methods to identify one or more hybridomas which produce an antibody which specifically binds with the marker protein or a fragment thereof. There is also provided herein hybridomas made by this method and antibodies made using such hybridomas.

Methods of Assessing Efficacy

There is also provided herein a method of assessing the efficacy of a test compound for inhibiting disease cells. As described above, differences in the level of expression of the markers correlate with the abnormal state of the subject's cells. Although it is recognized that changes in the levels of expression of certain of the markers likely result from the abnormal state of such cells, it is likewise recognized that changes in the levels of expression of other of the markers induce, maintain, and promote the abnormal state of those cells. Thus, compounds which inhibit a disorder and/or disease state in a subject will cause the level of expression of one or more of the markers to change to a level nearer the normal level of expression for that marker (i.e. the level of expression for the marker in normal cells).

This method thus comprises comparing expression of a marker in a first cell sample and maintained in the presence of the test compound and expression of the marker in a second cell sample and maintained in the absence of the test compound. A significantly reduced expression of a marker in the presence of the test compound is an indication that the test compound inhibits a related disease. The cell samples may, for example, be aliquots of a single sample of normal cells obtained from a subject, pooled samples of normal cells obtained from a subject, cells of a normal cell line, aliquots of a single sample of related disease cells obtained from a subject, pooled samples of related disease cells obtained from a subject, cells of a related disease cell line, or the like.

In one embodiment, the samples are cancer-related disease cells obtained from a subject and a plurality of compounds believed to be effective for inhibiting various cancer-related diseases are tested in order to identify the compound which is likely to best inhibit the cancer-related disease in the subject.

This method may likewise be used to assess the efficacy of a therapy for inhibiting a related disease in a subject. In this method, the level of expression of one or more markers in a pair of samples (one subjected to the therapy, the other not subjected to the therapy) is assessed. As with the method of assessing the efficacy of test compounds, if the therapy induces a significantly lower level of expression of a marker then the therapy is efficacious for inhibiting a cancer-related disease. As above, if samples from a selected subject are used in this method, then alternative therapies can be assessed in vitro in order to select a therapy most likely to be efficacious for inhibiting a cancer-related disease in the subject.

As described herein, the abnormal state of human cells is correlated with changes in the levels of expression of the markers. There is also provided a method for assessing the harmful potential of a test compound. This method comprises maintaining separate aliquots of human cells in the presence and absence of the test compound. Expression of a marker in each of the aliquots is compared. A significantly higher level of expression of a marker in the aliquot maintained in the presence of the test compound (relative to the aliquot maintained in the absence of the test compound) is an indication that the test compound possesses a harmful potential. The relative harmful potential of various test compounds can be assessed by comparing the degree of enhancement or inhibition of the level of expression of the relevant markers, by comparing the number of markers for which the level of expression is enhanced or inhibited, or by comparing both. Various aspects are described in further detail in the following subsections.

Isolated Proteins and Antibodies

One aspect pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein").

When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein. In certain embodiments, useful proteins are substantially identical (e.g., at least about 40%, and in certain embodiments, 50%, 60%, 70%, 80%, 90%, 95%, or 99%) to one of these sequences and retain the functional activity of the corresponding naturally-occurring marker protein yet differ in amino acid sequence due to natural allelic variation or mutagenesis.

In addition, libraries of segments of a marker protein can be used to generate a variegated population of polypeptides for screening and subsequent selection of variant marker proteins or segments thereof.

Predictive Medicine

There is also provided herein uses of the animal models and markers in the field of predictive medicine in which diagnostic assays, prognostic assays, pharmacogenomics, and monitoring clinical trials are used for prognostic (predictive) purposes to thereby treat an individual prophylactically. Accordingly, there is also provided herein diagnostic assays for determining the level of expression of one or more marker proteins or nucleic acids, in order to determine whether an individual is at risk of developing a particular disorder and/or disease. Such assays can be used for prognostic or predictive purposes to thereby prophylactically treat an individual prior to the onset of the disorder and/or disease.

In another aspect, the methods are useful for at least periodic screening of the same individual to see if that individual has been exposed to chemicals or toxins that change his/her expression patterns.

Yet another aspect pertains to monitoring the influence of agents (e.g., drugs or other compounds) administered either to inhibit a disorder and/or disease or to treat or prevent any other disorder (e.g., in order to understand any system effects that such treatment may have) on the expression or activity of a marker in clinical trials.

Pharmaceutical Compositions

The compounds may be in a formulation for administration topically, locally or systemically in a suitable pharmaceutical carrier. Remington's Pharmaceutical Sciences, 15th Edition by E. W. Martin (Mark Publishing Company, 1975), discloses typical carriers and methods of preparation. The compound may also be encapsulated in suitable biocompatible microcapsules, microparticles or microspheres formed of biodegradable or non-biodegradable polymers or proteins or liposomes for targeting to cells. Such systems are well known to those skilled in the art and may be optimized for use with the appropriate nucleic acid.

Various methods for nucleic acid delivery are described, for example in Sambrook et al., 1989, Molecular Cloning: A Laboratory Manual, Cold Spring Harbor Laboratory, New York; and Ausubel et al., 1994, Current Protocols in Molecular Biology, John Wiley & Sons, New York. Such nucleic acid delivery systems comprise the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition. The nucleic acid delivery system can be provided to the cell either directly, such as by contacting it with the cell, or indirectly, such as through the action of any biological process.

Formulations for topical administration may include ointments, lotions, creams, gels, drops, suppositories, sprays, liquids and powders. Conventional pharmaceutical carriers, aqueous, powder or oily bases, or thickeners can be used as desired.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, with an added preservative. Those of skill in the art can readily determine the various parameters for preparing and formulating the compositions without resort to undue experimentation. The compound can be used alone or in combination with other suitable components.

In general, methods of administering compounds, including nucleic acids, are well known in the art. In particular, the routes of administration already in use for nucleic acid therapeutics, along with formulations in current use, provide preferred routes of administration and formulation for the nucleic acids selected will depend of course, upon factors such as the particular formulation, the severity of the state of the subject being treated, and the dosage required for therapeutic efficacy. As generally used herein, an "effective amount" is that amount which is able to treat one or more symptoms of the disorder, reverse the progression of one or more symptoms of the disorder, halt the progression of one or more symptoms of the disorder, or prevent the occurrence of one or more symptoms of the disorder in a subject to whom the formulation is administered, as compared to a matched subject not receiving the compound. The actual effective amounts of compound can vary according to the specific compound or combination thereof being utilized, the particular composition formulated, the mode of administration, and the age, weight, condition of the individual, and severity of the symptoms or condition being treated.

Any acceptable method known to one of ordinary skill in the art may be used to administer a formulation to the subject. The administration may be localized (i.e., to a particular region, physiological system, tissue, organ, or cell type) or systemic, depending on the condition being treated.

Pharmacogenomics

The markers are also useful as pharmacogenomic markers. As used herein, a "pharmacogenomic marker" is an objective biochemical marker whose expression level correlates with a specific clinical drug response or susceptibility in a subject. The presence or quantity of the pharmacogenomic marker expression is related to the predicted response of the subject and more particularly the subject's tumor to therapy with a specific drug or class of drugs. By assessing the presence or quantity of the expression of one or more pharmacogenomic markers in a subject, a drug therapy which is most appropriate for the subject, or which is predicted to have a greater degree of success, may be selected.

Monitoring Clinical Trials

Monitoring the influence of agents (e.g., drug compounds) on the level of expression of a marker can be applied not only in basic drug screening, but also in clinical trials. For example, the effectiveness of an agent to affect marker expression can be monitored in clinical trials of subjects receiving treatment for a cancer-related disease.

In one non-limiting embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of:

i) obtaining a pre-administration sample from a subject prior to administration of the agent;

ii) detecting the level of expression of one or more selected markers in the pre-administration sample;

iii) obtaining one or more post-administration samples from the subject;

iv) detecting the level of expression of the marker(s) in the post-administration samples;

v) comparing the level of expression of the marker(s) in the pre-administration sample with the level of expression of the marker(s) in the post-administration sample or samples; and vi) altering the administration of the agent to the subject accordingly.

For example, increased expression of the marker gene(s) during the course of treatment may indicate ineffective dosage and the desirability of increasing the dosage. Conversely, decreased expression of the marker gene(s) may indicate efficacious treatment and no need to change dosage.

Electronic Apparatus Readable Media, Systems, Arrays and Methods of Using Same

As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; and general hard disks and hybrids of these categories such as magnetic/optical storage media. The medium is adapted or configured for having recorded thereon a marker as described herein.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as personal digital assistants (PDAs), cellular phone, pager and the like; and local and distributed processing systems.

As used herein, "recorded" refers to a process for storing or encoding information on the electronic apparatus readable medium. Those skilled in the art can readily adopt any method for recording information on media to generate materials comprising the markers described herein.

A variety of software programs and formats can be used to store the marker information of the present invention on the electronic apparatus readable medium. Any number of data processor structuring formats (e.g., text file or database) may be employed in order to obtain or create a medium having recorded thereon the markers. By providing the markers in readable form, one can routinely access the marker sequence information for a variety of purposes. For example, one skilled in the art can use the nucleotide or amino acid sequences in readable form to compare a target sequence or target structural motif with the sequence information stored within the data storage means. Search means are used to identify fragments or regions of the sequences which match a particular target sequence or target motif.

Thus, there is also provided herein a medium for holding instructions for performing a method for determining whether a subject has a cancer-related disease or a predisposition to a cancer-related disease, wherein the method comprises the steps of determining the presence or absence of a marker and based on the presence or absence of the marker, determining whether the subject has a cancer-related disease or a pre-disposition to a cancer-related disease and/or recommending a particular treatment for a cancer-related disease or pre-cancer-related disease condition.

There is also provided herein an electronic system and/or in a network, a method for determining whether a subject has a cancer-related disease or a pre-disposition to a cancer-related disease associated with a marker wherein the method comprises the steps of determining the presence or absence of the marker, and based on the presence or absence of the marker, determining whether the subject has a particular disorder and/or disease or a pre-disposition to such disorder and/or disease, and/or recommending a particular treatment for such disease or disease and/or such pre-cancer-related disease condition. The method may further comprise the step of receiving phenotypic information associated with the subject and/or acquiring from a network phenotypic information associated with the subject.

Also provided herein is a network, a method for determining whether a subject has a disorder and/or disease or a pre-disposition to a disorder and/or disease associated with a marker, the method comprising the steps of receiving information associated with the marker, receiving phenotypic information associated with the subject, acquiring information from the network corresponding to the marker and/or disorder and/or disease, and based on one or more of the phenotypic information, the marker, and the acquired information, determining whether the subject has a disorder and/or disease or a pre-disposition thereto. The method may further comprise the step of recommending a particular treatment for the disorder and/or disease or pre-disposition thereto.

There is also provided herein a business method for determining whether a subject has a disorder and/or disease or a pre-disposition thereto, the method comprising the steps of receiving information associated with the marker, receiving phenotypic information associated with the subject, acquiring information from the network corresponding to the marker and/or a disorder and/or disease, and based on one or more of the phenotypic information, the marker, and the acquired information, determining whether the subject has a disorder and/or disease or a pre-disposition thereto. The method may further comprise the step of recommending a particular treatment therefor.

There is also provided herein an array that can be used to assay expression of one or more genes in the array. In one embodiment, the array can be used to assay gene expression in a tissue to ascertain tissue specificity of genes in the array. In this manner, up to about 7000 or more genes can be simultaneously assayed for expression. This allows a profile to be developed showing a battery of genes specifically expressed in one or more tissues.

In addition to such qualitative determination, there is provided herein the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined.

Such a determination is useful, for example, to know the effect of cell-cell interaction at the level of gene expression. If an agent is administered therapeutically to treat one cell type but has an undesirable effect on another cell type, the method provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a disorder and/or disease, progression thereof, and processes, such as cellular transformation associated therewith.

The array is also useful for ascertaining the effect of the expression of a gene or the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

Surrogate Markers

The markers may serve as surrogate markers for one or more disorders or disease states or for conditions leading up thereto. As used herein, a "surrogate marker" is an objective biochemical marker which correlates with the absence or presence of a disease or disorder, or with the progression of a disease or disorder. The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies, or when an assessment of disease progression is desired before a potentially dangerous clinical endpoint is reached.

The markers are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo.

Pharmacodynamic markers are of particular use in increasing the sensitivity of detection of drug effects, particularly when the drug is administered in low doses. Since even a small amount of a drug may be sufficient to activate multiple rounds of marker transcription or expression, the amplified marker may be in a quantity which is more readily detectable than the drug itself. Also, the marker may be more easily detected due to the nature of the marker itself; for example, using the methods described herein, antibodies may be employed in an immune-based detection system for a protein marker, or marker-specific radiolabeled probes may be used to detect a mRNA marker. Furthermore, the use of a pharmacodynamic marker may offer mechanism-based prediction of risk due to drug treatment beyond the range of possible direct observations.

Protocols for Testing

The method of testing for a disorder and/or disease may comprise, for example measuring the expression level of each marker gene in a biological sample from a subject over time and comparing the level with that of the marker gene in a control biological sample.

When the marker gene is one of the genes described herein and the expression level is differentially expressed (for examples, higher or lower than that in the control), the subject is judged to be affected with a disorder and/or disease. When the expression level of the marker gene falls within the permissible range, the subject is unlikely to be affected therewith.

The standard value for the control may be pre-determined by measuring the expression level of the marker gene in the control, in order to compare the expression levels. For example, the standard value can be determined based on the expression level of the above-mentioned marker gene in the control. For example, in certain embodiments, the permissible range is taken as ±2 S.D. based on the standard value. Once the standard value is determined, the testing method may be performed by measuring only the expression level in a biological sample from a subject and comparing the value with the determined standard value for the control.

Expression levels of marker genes include transcription of the marker genes to mRNA, and translation into proteins. Therefore, one method of testing for a disorder and/or disease is performed based on a comparison of the intensity of expression of mRNA corresponding to the marker genes, or the expression level of proteins encoded by the marker genes.

The measurement of the expression levels of marker genes in the testing for a disorder and/or disease can be carried out according to various gene analysis methods. Specifically, one can use, for example, a hybridization technique using nucleic acids that hybridize to these genes as probes, or a gene amplification technique using DNA that hybridize to the marker genes as primers.

The probes or primers used for the testing can be designed based on the nucleotide sequences of the marker genes. The identification numbers for the nucleotide sequences of the respective marker genes are described herein.

Further, it is to be understood that genes of higher animals generally accompany polymorphism in a high frequency. There are also many molecules that produce isoforms comprising mutually different amino acid sequences during the splicing process. Any gene associated with a cancer-related disease that has an activity similar to that of a marker gene is included in the marker genes, even if it has nucleotide sequence differences due to polymorphism or being an isoform.

It is also to be understood that the marker genes can include homologs of other species in addition to humans. Thus, unless otherwise specified, the expression "marker gene" refers to a homolog of the marker gene unique to the species or a foreign marker gene which has been introduced into an individual.

Also, it is to be understood that a "homolog of a marker gene" refers to a gene derived from a species other than a human, which can hybridize to the human marker gene as a probe under stringent conditions. Such stringent conditions are known to one skilled in the art who can select an appropriate condition to produce an equal stringency experimentally or empirically.

A polynucleotide comprising the nucleotide sequence of a marker gene or a nucleotide sequence that is complementary to the complementary strand of the nucleotide sequence of a marker gene and has at least 15 nucleotides, can be used as a primer or probe. Thus, a "complementary strand" means one strand of a double stranded DNA with respect to the other strand and which is composed of A:T (U for RNA) and G:C base pairs.

In addition, "complementary" means not only those that are completely complementary to a region of at least 15 continuous nucleotides, but also those that have a nucleotide sequence homology of at least 40% in certain instances, 50% in certain instances, 60% in certain instances, 70% in certain instances, 80% in certain instances, 90% in certain instances, and 95% in certain instances, or higher. The degree of homology between nucleotide sequences can be determined by an algorithm, BLAST, etc.

Such polynucleotides are useful as a probe to detect a marker gene, or as a primer to amplify a marker gene. When used as a primer, the polynucleotide comprises usually 15 bp to 100 bp, and in certain embodiments 15 by to 35 by of nucleotides. When used as a probe, a DNA comprises the whole nucleotide sequence of the marker gene (or the complementary strand thereof), or a partial sequence thereof that has at least 15 by nucleotides. When used as a primer, the 3' region must be complementary to the marker gene, while the 5' region can be linked to a restriction enzyme-recognition sequence or a tag.

"Polynucleotides" may be either DNA or RNA. These polynucleotides may be either synthetic or naturally-occurring. Also, DNA used as a probe for hybridization is usually labeled. Those skilled in the art readily understand such labeling methods. Herein, the term "oligonucleotide" means a polynucleotide with a relatively low degree of polymerization. Oligonucleotides are included in polynucleotides.

Tests for a disorder and/or disease using hybridization techniques can be performed using, for example, Northern hybridization, dot blot hybridization, or the DNA microarray technique. Furthermore, gene amplification techniques, such as the RT-PCR method may be used. By using the PCR amplification monitoring method during the gene amplification step in RT-PCR, one can achieve a more quantitative analysis of the expression of a marker gene.

In the PCR gene amplification monitoring method, the detection target (DNA or reverse transcript of RNA) is hybridized to probes that are labeled with a fluorescent dye and a quencher which absorbs the fluorescence. When the PCR proceeds and Taq polymerase degrades the probe with its 5'-3' exonuclease activity, the fluorescent dye and the quencher draw away from each other and the fluorescence is detected. The fluorescence is detected in real time. By simultaneously measuring a standard sample in which the copy number of a target is known, it is possible to determine the copy number of the target in the subject sample with the cycle number where PCR amplification is linear. Also, one skilled in the art recognizes that the PCR amplification monitoring method can be carried out using any suitable method.

The method of testing for a cancer-related disease can be also carried out by detecting a protein encoded by a marker gene. Hereinafter, a protein encoded by a marker gene is described as a "marker protein." For such test methods, for example, the Western blotting method, the immunoprecipitation method, and the ELISA method may be employed using an antibody that binds to each marker protein.

Antibodies used in the detection that bind to the marker protein may be produced by any suitable technique. Also, in order to detect a marker protein, such an antibody may be appropriately labeled. Alternatively, instead of labeling the antibody, a substance that specifically binds to the antibody, for example, protein A or protein G, may be labeled to detect the marker protein indirectly. More specifically, such a detection method can include the ELISA method.

A protein or a partial peptide thereof used as an antigen may be obtained, for example, by inserting a marker gene or a portion thereof into an expression vector, introducing the construct into an appropriate host cell to produce a transformant, culturing the transformant to express the recombinant protein, and purifying the expressed recombinant protein from the culture or the culture supernatant. Alternatively, the amino acid sequence encoded by a gene or an oligopeptide comprising a portion of the amino acid sequence encoded by a full-length cDNA are chemically synthesized to be used as an immunogen.

Furthermore, a test for a cancer-related disease can be performed using as an index not only the expression level of a marker gene but also the activity of a marker protein in a biological sample. Activity of a marker protein means the biological activity intrinsic to the protein. Various methods can be used for measuring the activity of each protein.

Even if a subject is not diagnosed as being affected with a disorder and/or disease in a routine test in spite of symptoms suggesting these diseases, whether or not such a subject is suffering from a disorder and/or disease can be easily determined by performing a test according to the methods described herein.

More specifically, in certain embodiments, when the marker gene is one of the genes described herein, an increase or decrease in the expression level of the marker gene in a subject whose symptoms suggest at least a susceptibility to a disorder and/or disease indicates that the symptoms are primarily caused thereby.

In addition, the tests are useful to determine whether a disorder and/or disease are improving in a subject. In other words, the methods described herein can be used to judge the therapeutic effect of a treatment therefor. Furthermore, when the marker gene is one of the genes described herein, an increase or decrease in the expression level of the marker gene in a subject, who has been diagnosed as being affected thereby, implies that the disease has progressed more.

The severity and/or susceptibility to a disorder and/or disease may also be determined based on the difference in expression levels. For example, when the marker gene is one of the genes described herein, the degree of increase in the expression level of the marker gene is correlated with the presence and/or severity of a disorder and/or disease.

Animal Models

Animal models for a disorder and/or disease where the expression level of one or more marker genes or a gene functionally equivalent to the marker gene has been elevated in the animal model can also be made. A "functionally equivalent gene" as used herein generally is a gene that encodes a protein having an activity similar to a known activity of a protein encoded by the marker gene. A representative example of a functionally equivalent gene includes a counterpart of a marker gene of a subject animal, which is intrinsic to the animal.

The animal model is useful for detecting physiological changes due to a disorder and/or disease. In certain embodiments, the animal model is useful to reveal additional functions of marker genes and to evaluate drugs whose targets are the marker genes.

An animal model can be created by controlling the expression level of a counterpart gene or administering a counterpart gene. The method can include creating an animal model by controlling the expression level of a gene selected from the group of genes described herein. In another embodiment, the method can include creating an animal model by administering the protein encoded by a gene described herein, or administering an antibody against the protein. It is to be also understood, that in certain other embodiments, the marker can be over-expressed such that the marker can then be measured using appropriate methods. In another embodiment, an animal model can be created by introducing a gene selected from such groups of genes, or by administering a protein encoded by such a gene. In another embodiment, a disorder and/or disease can be induced by suppressing the expression of a gene selected from such groups of genes or the activity of a protein encoded by such a gene. An antisense nucleic acid, a ribozyme, or an RNAi can be used to suppress the expression. The activity of a protein can be controlled effectively by administering a substance that inhibits the activity, such as an antibody.

The animal model is useful to elucidate the mechanism underlying a disorder and/or disease and also to test the safety of compounds obtained by screening. For example, when an animal model develops the symptoms of a particular disorder and/or disease, or when a measured value involved in certain a disorder and/or disease alters in the animal, a screening system can be constructed to explore compounds having activity to alleviate the disease.

As used herein, the expression "an increase in the expression level" refers to any one of the following: where a marker gene introduced as a foreign gene is expressed artificially; where the transcription of a marker gene intrinsic to the subject animal and the translation thereof into the protein are enhanced; or where the hydrolysis of the protein, which is the translation product, is suppressed.

As used herein, the expression "a decrease in the expression level" refers to either the state in which the transcription of a marker gene of the subject animal and the translation thereof into the protein are inhibited, or the state in which the hydrolysis of the protein, which is the translation product, is enhanced. The expression level of a gene can be determined, for example, by a difference in signal intensity on a DNA chip. Furthermore, the activity of the translation product—the protein—can be determined by comparing with that in the normal state.

It is also within the contemplated scope that the animal model can include transgenic animals, including, for example animals where a marker gene has been introduced and expressed artificially; marker gene knockout animals; and knock-in animals in which another gene has been substituted for a marker gene. A transgenic animal, into which an antisense nucleic acid of a marker gene, a ribozyme, a polynucleotide having an RNAi effect, or a DNA functioning as a decoy nucleic acid or such has been introduced, can be used as the transgenic animal. Such transgenic animals also include, for example, animals in which the activity of a marker protein has been enhanced or suppressed by introducing a mutation(s) into the coding region of the gene, or the amino acid sequence has been modified to become resistant or susceptible to hydrolysis. Mutations in an amino acid sequence include substitutions, deletions, insertions, and additions.

Examples of Expression

In addition, the expression itself of a marker gene can be controlled by introducing a mutation(s) into the transcriptional regulatory region of the gene. Those skilled in the art understand such amino acid substitutions. Also, the number of amino acids that are mutated is not particularly restricted, as long as the activity is maintained. Normally, it is within 50 amino acids, in certain non-limiting embodiments, within 30 amino acids, within 10 amino acids, or within 3 amino acids. The site of mutation may be any site, as long as the activity is maintained.

In yet another aspect, there is provided herein screening methods for candidate compounds for therapeutic agents to treat a particular disorder and/or disease. One or more marker genes are selected from the group of genes described herein. A therapeutic agent for a cancer-related disease can be obtained by selecting a compound capable of increasing or decreasing the expression level of the marker gene(s).

It is to be understood that the expression "a compound that increases the expression level of a gene" refers to a compound that promotes any one of the steps of gene transcription, gene translation, or expression of a protein activity. On the other hand, the expression "a compound that decreases the expression level of a gene", as used herein, refers to a compound that inhibits any one of these steps.

In particular aspects, the method of screening for a therapeutic agent for a disorder and/or disease can be carried out either in vivo or in vitro. This screening method can be performed, for example, by:

1) administering a candidate compound to an animal subject;

2) measuring the expression level of a marker gene(s) in a biological sample from the animal subject; or 3) selecting a compound that increases or decreases the expression level of a marker gene(s) as compared to that in a control with which the candidate compound has not been contacted.

In still another aspect, there is provided herein a method to assess the efficacy of a candidate compound for a pharmaceutical agent on the expression level of a marker gene(s) by contacting an animal subject with the candidate compound and monitoring the effect of the compound on the expression level of the marker gene(s) in a biological sample derived from the animal subject. The variation in the expression level of the marker gene(s) in a biological sample derived from the animal subject can be monitored using the same technique as used in the testing method described above. Furthermore, based on the evaluation, a candidate compound for a pharmaceutical agent can be selected by screening.

All patents, patent applications and references cited herein are incorporated in their entirety by reference. While the invention has been described and exemplified in sufficient detail for those skilled in this art to make and use it, various alternatives, modifications and improvements should be apparent without departing from the spirit and scope of the invention. One skilled in the art readily appreciates that the present invention is well adapted to carry out the objects and obtain the ends and advantages mentioned, as well as those inherent therein.

Certain Nucleobase Sequences

Nucleobase sequences of mature miRNAs and their corresponding stem-loop sequences described herein are the sequences found in miRBase, an online searchable database of miRNA sequences and annotation, found at http://micro-rna.sanger.ac.uk/. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence. The compounds that may encompass such modified oligonucleotides may be complementary to any nucleobase sequence version of the miRNAs described herein.

It is understood that any nucleobase sequence set forth herein is independent of any modification to a sugar moiety, an internucleoside linkage, or a nucleobase. It is further understood that a nucleobase sequence comprising U's also encompasses the same nucleobase sequence wherein 'U' is replaced by 'T' at one or more positions having 'U'. Conversely, it is understood that a nucleobase sequence comprising T's also encompasses the same nucleobase sequence wherein 'T' is replaced by 'U' at one or more positions having 'T'.

In certain embodiments, a modified oligonucleotide has a nucleobase sequence that is complementary to a miRNA or a precursor thereof, meaning that the nucleobase sequence of a modified oligonucleotide is a least 60%, 65%, 70%, 75%, 80%, 85%, 90%, 95%, 97%, 98% or 99% identical to the complement of a miRNA or precursor thereof over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the two sequences hybridize under stringent hybridization conditions. Accordingly, in certain embodiments the nucleobase sequence of a modified oligonucleotide may have one or more mismatched base-pairs with respect to its target miRNA or target miRNA precursor sequence, and is capable of hybridizing to its target sequence. In certain embodiments, a modified oligonucleotide has a nucleobase sequence that is 100% complementary to a miRNA or a precursor thereof. In certain embodiments, the nucleobase sequence of a modified oligonucleotide has full-length complementary to a miRNA.

miRNA (miR) Therapies

In some embodiments, the present invention provides microRNAs that inhibit the expression of one or more genes in a subject. MicroRNA expression profiles can serve as a new class of cancer biomarkers.

Included herein are methods of inhibiting gene expression and/or activity using one or more MiRs. In some embodiments, the miR(s) inhibit the expression of a protein. In other embodiments, the miRNA(s) inhibits gene activity (e.g., cell invasion activity).

The miRNA can be isolated from cells or tissues, recombinantly produced, or synthesized in vitro by a variety of techniques well known to one of ordinary skill in the art. In one embodiment, miRNA is isolated from cells or tissues. Techniques for isolating miRNA from cells or tissues are well known to one of ordinary skill in the art. For example, miRNA can be isolated from total RNA using the mirVana miRNA isolation kit from Ambion, Inc. Another technique utilizes the flashIPAGE™ Fractionator System (Ambion, Inc.) for PAGE purification of small nucleic acids.

For the use of miRNA therapeutics, it is understood by one of ordinary skill in the art that nucleic acids administered in vivo are taken up and distributed to cells and tissues.

The nucleic acid may be delivered in a suitable manner which enables tissue-specific uptake of the agent and/or nucleic acid delivery system. The formulations described herein can supplement treatment conditions by any known conventional therapy, including, but not limited to, antibody administration, vaccine administration, administration of cytotoxic agents, natural amino acid polypeptides, nucleic acids, nucleotide analogues, and biologic response modifiers. Two or more combined compounds may be used together or sequentially.

Certain embodiments of the invention provide pharmaceutical compositions containing (a) one or more nucleic acid or small molecule compounds and (b) one or more other chemotherapeutic agents.

Additional Useful Definitions

"Subject" means a human or non-human animal selected for treatment or therapy. "Subject suspected of having" means a subject exhibiting one or more clinical indicators of a disorder, disease or condition.

"Preventing" or "prevention" refers to delaying or forestalling the onset, development or progression of a condition or disease for a period of time, including weeks, months, or years. "Treatment" or "treat" means the application of one or more specific procedures used for the cure or amelioration of a disorder and/or disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Subject in need thereof" means a subject identified as in need of a therapy or treatment.

"Administering" means providing a pharmaceutical agent or composition to a subject, and includes, but is not limited to, administering by a medical professional and self-administering.

"Parenteral administration" means administration through injection or infusion. Parenteral administration includes, but is not limited to, subcutaneous administration, intravenous administration, intramuscular administration, intra-arterial administration, and intracranial administration. "Subcutaneous administration" means administration just below the skin.

"Improves function" means the changes function toward normal parameters. In certain embodiments, function is assessed by measuring molecules found in a subject's bodily fluids. Pharmaceutical composition" means a mixture of substances suitable for administering to an individual that includes a pharmaceutical agent. For example, a pharmaceutical composition may comprise a modified oligonucleotide and a sterile aqueous solution.

"Target nucleic acid," "target RNA," "target RNA transcript" and "nucleic acid target" all mean a nucleic acid capable of being targeted by antisense compounds. Targeting" means the process of design and selection of nucleobase sequence that will hybridize to a target nucleic acid and induce a desired effect. "Targeted to" means having a nucleobase sequence that will allow hybridization to a target nucleic acid to induce a desired effect. In certain embodiments, a desired effect is reduction of a target nucleic acid.

"Modulation" means to a perturbation of function or activity. In certain embodiments, modulation means an increase in gene expression. In certain embodiments, modulation means a decrease in gene expression.

"Expression" means any functions and steps by which a gene's coded information is converted into structures present and operating in a cell.

"Region" means a portion of linked nucleosides within a nucleic acid. In certain embodiments, a modified oligonucleotide has a nucleobase sequence that is complementary to a region of a target nucleic acid. For example, in certain such embodiments a modified oligonucleotide is complementary to a region of a miRNA stem-loop sequence. In certain such embodiments, a modified oligonucleotide is 100% identical to a region of a miRNA sequence.

"Segment" means a smaller or sub-portion of a region.

"Nucleobase sequence" means the order of contiguous nucleobases, in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding. "Complementary" means a first nucleobase sequence is at least 60%, 65%, 70%, 75%, 80%, 85%, 90%, 95%, 97%, 98% or 99% identical, or is 100% identical, to the complement of a second nucleobase sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the two sequences hybridize under stringent hybridization conditions. In certain embodiments a modified oligonucleotide that has a nucleobase sequence which is 100% complementary to a miRNA, or precursor thereof, may not be 100% complementary to the miRNA, or precursor thereof, over the entire length of the modified oligonucleotide.

"Complementarity" means the nucleobase pairing ability between a first nucleic acid and a second nucleic acid. "Full-length complementarity" means each nucleobase of a first nucleic acid is capable of pairing with each nucleobase at a corresponding position in a second nucleic acid. For example, in certain embodiments, a modified oligonucleotide wherein each nucleobase has complementarity to a nucleobase in an miRNA has full-length complementarity to the miRNA.

"Percent complementary" means the number of complementary nucleobases in a nucleic acid divided by the length of the nucleic acid. In certain embodiments, percent complementarity of a modified oligonucleotide means the number of nucleobases that are complementary to the target nucleic acid, divided by the number of nucleobases of the modified oligonucleotide. In certain embodiments, percent complementarity of a modified oligonucleotide means the number of nucleobases that are complementary to a miRNA, divided by the number of nucleobases of the modified oligonucleotide.

"Percent region bound" means the percent of a region complementary to an oligonucleotide region. Percent region bound is calculated by dividing the number of nucleobases of the target region that are complementary to the oligonucleotide by the length of the target region. In certain embodiments, percent region bound is at least 80%, at least 85%, at least 90%, at least 95%, at least 96%, at least 97%, at least 98%, at least 99%, or 100%.

"Percent identity" means the number of nucleobases in first nucleic acid that are identical to nucleobases at corresponding positions in a second nucleic acid, divided by the total number of nucleobases in the first nucleic acid.

"Substantially identical" used herein may mean that a first and second nucleobase sequence are at least 60%, 65%, 70%, 75%, 80%, 85%, 90%, 95%, 97%, 98% or 99% identical, or 100% identical, over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Non-complementary nucleobase" means two nucleobases that are not capable of pairing through hydrogen bonding.

"Identical" means having the same nucleobase sequence.

"miRNA" or "miR" means a non-coding RNA between 18 and 25 nucleobases in length which hybridizes to and regulates the expression of a coding RNA. In certain embodiments, a miRNA is the product of cleavage of a pre-miRNA by the enzyme Dicer. Examples of miRNAs are found in the miRNA database known as miRBase (http://microma.sanger.ac.uk/).

"Pre-miRNA" or "pre-miR" means a non-coding RNA having a hairpin structure, which contains a miRNA. In certain embodiments, a pre-miRNA is the product of cleavage of a pri-miR by the double-stranded RNA-specific ribonuclease known as Drosha.

"Stem-loop sequence" means an RNA having a hairpin structure and containing a mature miRNA sequence. Pre-miRNA sequences and stem-loop sequences may overlap. Examples of stem-loop sequences are found in the miRNA database known as miRBase (microrna.sanger.ac.uk/.

"miRNA precursor" means a transcript that originates from a genomic DNA and that comprises a non-coding, structured RNA comprising one or more miRNA sequences. For example, in certain embodiments a miRNA precursor is a pre-miRNA. In certain embodiments, a miRNA precursor is a pri-miRNA.

"Antisense compound" means a compound having a nucleobase sequence that will allow hybridization to a target nucleic acid. In certain embodiments, an antisense compound is an oligonucleotide having a nucleobase sequence complementary to a target nucleic acid.

"Oligonucleotide" means a polymer of linked nucleosides, each of which can be modified or unmodified, independent from one another. "Naturally occurring internucleoside linkage" means a 3' to 5' phosphodiester linkage between nucleosides. "Natural nucleobase" means a nucleobase that is unmodified relative to its naturally occurring form. "miR antagonist"+means an agent designed to interfere with or inhibit the activity of a miRNA. In certain embodiments, a miR antagonist comprises an antisense compound targeted to a miRNA. In certain embodiments, a miR antagonist comprises a modified oligonucleotide having a nucleobase sequence that is complementary to the nucleobase sequence of a miRNA, or a precursor thereof. In certain embodiments, an miR antagonist comprises a small molecule, or the like that interferes with or inhibits the activity of an miRNA.

The methods and reagents described herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims. It will also be readily apparent to a person skilled in the art that varying substitutions and modifications may be made to the invention disclosed herein without departing from the scope and spirit of the invention.

It should be understood that although the present invention has been specifically disclosed by preferred embodiments and optional features, modifications and variations of the concepts herein disclosed may be resorted to by those skilled in the art, and that such modifications and variations are considered to be within the scope of this invention as defined by the appended claims.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

REFERENCES

The publication and other material used herein to illuminate the invention or provide additional details respecting the practice of the invention, are incorporated by reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

1. Jemal A, Siegel R, Ward E, et al. Cancer statistics. CA Cancer J Clin 2008; 58(2):71-96.
2. Cannistra S A. Cancer of the ovary. N Engl J Med 2004; 351(24):2519-29.
3. Myers E R, Bastian L A, Havrilesky L J, et al. Management of adnexal masses. Evid Rep/Technol Assess 2006 (130):1-145.
4. Jacobs I J, Menon U. Progress and challenges in screening for early detection of ovarian cancer. Mol Cell Proteomics 2004; 3(4):355-66.
5. Jacobs I, Davies A P, Bridge J, et al. Prevalence screening for ovarian cancer in post-menopausal women by CA-125 measurement and ultrasonography. BMJ 1993; 306:1030-4.
6. Olivier R I, Lubsen-Brandsma M A, Verhoef S, van Beurden M. CA125 and transvaginal ultrasound monitoring in high-risk women cannot prevent the diagnosis of advanced ovarian cancer. Gynecol Oncol 2006; 100(1): 20-6.
7. Jannot G, Simard M J. Tumor-related microRNAs functions in *Caenorhabditis elegans*. Oncogene 2006; 25(46): 6197-201.
8. Johnson S M, Grosshans H, Shingara J, et al. RAS is regulated by the let-7 microRNA family. Cell 2005; 120(5):635-47.
9. Cimmino A, Calin G A, Fabbri M, et al. miR-15 and miR-16 induce apoptosis by targeting BCL2. Proc Natl Acad Sci USa 2005; 102(39): 13944-9.

10. Meng F, Henson R, Wehbe-Janek H, et al. MicroRNA-21 regulates expression of the PTEN tumor suppressor gene in human hepatocellular cancer. Gastroenterology 2007; 133(2):647-58.
11. Mendell J T. miRiad roles for the miR-17-92 cluster in development and disease. Cell 2008; 133(2):217-22.
12. Iorio M V, Visone R, Di Leva G, et al. MicroRNA signatures in human ovarian cancer. Cancer Res 2007; 67(18):8699-707.
13. Nam E J, Yoon H, Kim S W, et al. MicroRNA expression profiles in serous ovarian carcinoma. Clin Cancer Res 2008; 14(9):2690-5.
14. Zhang L, Volinia S, Bonome T, et al. Genomic and epigenetic alterations deregulate microRNA expression in human epithelial ovarian cancer. Proc Natl Acad Sci USA 2008; 105(19):7004-9.
15. Chim S S, Shing T K, Hung E C, et al. Detection and characterization of placental microRNAs in maternal plasma. Clin Chem 2008; 54(3):482-90.
16. Feng G, Li G, Gentil-Perret A, Tostain J, Genin C. Elevated serum-circulating RNA in patients with conventional renal cell cancer. Anticancer Res 2008; 28(1A): 321-6.
17. Lawrie C H, Gal S, Dunlop H M, et al. Detection of elevated levels of tumour-associated microRNAs in serum of patients with diffuse large B-cell lymphoma. Br J Haematol 2008; 141(5):672-5.
18. Taylor D D, Gercel-Taylor C. MicroRNA signatures of tumor-derived exosomes as diagnostic biomarkers of ovarian cancer. Gynecol Oncol 2008; 110(1):13-21.
19. Volinia S, Calin G A, Liu C G, et al. A microRNA expression signature of human solid tumors defines cancer gene targets. Proc Natl Acad Sci USA 2006; 103(7): 2257-61.
20. Chan J A, Krichevsky A M, Kosik K S. MicroRNA-21 is an anti apoptotic factor in human glioblastoma cells. Cancer Res 2005; 65:6029-33.
21. Zhu S, Wu H, Wu F, et al. MicroRNA-21 targets tumor suppressor genes in invasion and metastasis. Cell Res 2008; 18(3):350-9.
22. Secord A A, Lee P S, Darcy K M, et al, Gynecologic Oncology Group. Maspin expression in epithelial ovarian cancer and associations with poor prognosis: a gynecologic oncology group study. Gynecol Oncol 2006; 101 (3):390-7.
23. He L, Thomson J M, Hemann M T, et al. A microRNA polycistron as a potential human oncogene. Nature 2005; 435(7043):828-33.
24. Petrocca F, Visone R, Onelli M R, et al. E2F1-regulated microRNAs impair TGFbeta-dependent cell-cycle arrest and apoptosis in gastric cancer. Cancer Cell 2008; 13(3): 272-86.
25. Tavazoie S F, Alarcon C, Oskarsson T, et al. Endogenous human microRNAs that suppress breast cancer metastasis. Nature 2008; 451 (7175):147-52.
26. Fabbri M, Garzon R, Cimmino A, et al. MicroRNA-29 family reverts aberrant methylation in lung cancer by targeting DNA methyltransferases 3A and 3B. Proc Natl Acad Sci USA 2007; 104(40):15805-10.
27. Saito Y, Liang G, Egger G, et al. Specific activation of microRNA-127 with downregulation of the proto-oncogene BCL6 by chromatin-modifying drugs in human cancer cells. Cancer Cell 2006; 9(6):435-43.
28. Tili E, Michaille J J, Calin G A. Expression and function of micro-RNAs in immune cells during normal or disease state. Int J Med Sci 2008; 5(2): 73-9.

What is claimed is:

1. A method of detecting an increased level of at least one miRNA biomarker in a subject having, or suspected of having, an epithelial ovarian cancer, comprising:
   determining whether the subject has CA-125 levels at or below 34 U/ml, and, when the subject has said CA-125 levels,
   obtaining a nucleic acid-containing test sample from the subject, wherein the test sample is extracted from serum;
   determining an expression profile of one or more microRNA biomarkers in the test sample, wherein the expression profile is determined by measuring the levels of one or more microRNA biomarkers in the test sample;
   comparing the expression profile of the one or more microRNA biomarkers in the test sample to a control level of miRNAs obtained from at least one control known to not have serous ovarian cancer, wherein the microRNA biomarkers comprise at least miR-92;
   detecting whether there is an increased level of the one or more miRNA biomarkers in the test sample as compared to a control level by contacting the test sample with at least one probe for at least one up-regulated miRNA and detecting binding between the probe and the up-regulated miRNA; and
   determining the presence of epithelial ovarian cancer in the subject, when the detecting of the one or more microRNA biomarkers indicates: a high level of the miR-92 biomarker in the test sample, relative to the level of a corresponding micro-RNA biomarker in the control.

2. The method of claim 1, further comprising: detecting at least one additional up-regulated micro-RNA biomarker selected from: miR-21 and miR-93, wherein miR-21 and miR-93 are over-expressed in the test sample, as compared to control levels.

3. The method of claim 2, further comprising:
   detecting a level of at least one down-regulated microRNA biomarker in the test sample that is less than the level of the corresponding micro-RNA biomarker in the control sample, wherein the at least one down-regulated micro-RNA biomarker is one or more of: miR-127, miR-155, and miR-99b.

4. A method of screening for one or more biomarkers for ovarian cancer in a subject, wherein the subject has normal CA-125 levels, comprising:
   obtaining a sample of serum from the subject,
   measuring CA-125 and, thereafter, when a measured CA-125 level is at or below 34 U/ml,
   conducting quantitative real-time polymerase chain reaction, and
   detecting whether there is an increased level of the one or more biomarkers in the serum sample of the subject as compared with a healthy control by contacting the serum sample with at least one probe for at least one up-regulated miRNA and detecting binding between the probe and the up-regulated miRNA, wherein the one or more biomarkers comprise miR-92, and
   determining the presence of epithelial ovarian cancer in the subject when the detecting of the one or more microRNA biomarkers indicates: a high level of the miR-92 biomarker in the serum sample, relative to the level of a corresponding biomarker in the control.

5. The method of claim 1, further comprising collecting a plurality of test samples from the subject at different time points and comparing the amount of the at least one biomarker in each test sample to determine if the amount of the at least one biomarker is increasing or decreasing in the subject over time.

6. The method of claim 1, wherein the control is an earlier sample from the subject.

7. The method of claim 1, wherein the detecting step comprises: amplification and quantification using real-time PCR microarray assay.

8. The method of claim 2, wherein a signature of up-regulated microRNAs is detected, wherein the signature consists of a combination of: miR-92, miR-21 and miR-93.

9. The method of claim 3, wherein a signature of down-regulated microRNAs is detected wherein the signature consists of a combination of: miR-127, miR-155 and miR-99b.

* * * * *